US008241854B2

(12) United States Patent
Yin et al.

(10) Patent No.: US 8,241,854 B2
(45) Date of Patent: *Aug. 14, 2012

(54) TRIGGERED RNAI

(75) Inventors: Peng Yin, Pasadena, CA (US); Niles A. Pierce, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/454,743

(22) Filed: May 22, 2009

(65) Prior Publication Data

US 2010/0035233 A1   Feb. 11, 2010

Related U.S. Application Data

(60) Provisional application No. 61/128,550, filed on May 22, 2008.

(51) Int. Cl.
    C12Q 1/68      (2006.01)
    C07H 21/02     (2006.01)
    C07H 21/04     (2006.01)
    C12N 15/11     (2006.01)
    C12N 15/00     (2006.01)

(52) U.S. Cl. ............... 435/6.11; 536/24.5; 536/23.1; 435/325; 514/44

(58) Field of Classification Search ........... 435/6, 91.31; 536/23.1, 24.5
    See application file for complete search history.

(56) References Cited

U.S. PATENT DOCUMENTS

| 4,714,680 | A  | 12/1987 | Civin |
| 4,897,355 | A  | 1/1990  | Eppstein et al. |
| 4,965,204 | A  | 10/1990 | Civin |
| 5,057,410 | A  | 10/1991 | Kawasaki et al. |
| 5,061,620 | A  | 10/1991 | Tsukamoto et al. |
| 5,459,127 | A  | 10/1995 | Felgner et al. |
| 5,579,793 | A  | 12/1996 | Gajewski et al. |
| 5,643,741 | A  | 7/1997  | Tsukamoto et al. |
| 5,677,136 | A  | 10/1997 | Simmons et al. |
| 5,716,827 | A  | 2/1998  | Tsukamoto et al. |
| 5,750,397 | A  | 5/1998  | Tsukamoto et al. |
| 5,928,913 | A  | 7/1999  | Efstathiou et al. |
| 5,989,823 | A  | 11/1999 | Jayasena et al. |
| 6,242,246 | B1 | 6/2001  | Gold et al. |
| 6,261,783 | B1 | 7/2001  | Jayasena et al. |
| 6,361,944 | B1 | 3/2002  | Mirkin et al. |
| 6,361,945 | B1 | 3/2002  | Becker et al. |
| 6,485,965 | B1 | 11/2002 | Klatzmann et al. |
| 6,506,559 | B1 | 1/2003  | Driver et al. |
| 6,555,367 | B1 | 4/2003  | Spence et al. |
| 6,899,871 | B2 | 5/2005  | Kasahara et al. |
| 7,033,834 | B2 | 4/2006  | Valerio et al. |
| 7,632,641 | B2 | 12/2009 | Dirks et al. |
| 7,727,721 | B2 | 6/2010  | Pierce et al. |
| 2002/0051769 | A1  | 5/2002  | Zhang |
| 2002/0172950 | A1  | 11/2002 | Kenny et al. |
| 2003/0092162 | A1  | 5/2003  | Shankara et al. |
| 2004/0009510 | A1* | 1/2004  | Seiwert et al. ............ 435/6 |
| 2004/0223953 | A1  | 11/2004 | Kung et al. |
| 2005/0239061 | A1* | 10/2005 | Marshall et al. ............ 435/6 |
| 2005/0260635 | A1  | 11/2005 | Dirks et al. |
| 2006/0035375 | A1* | 2/2006  | Head et al. ............ 435/383 |
| 2006/0088864 | A1* | 4/2006  | Smolke et al. ............ 435/6 |
| 2006/0228733 | A1  | 10/2006 | Pierce et al. |
| 2006/0234261 | A1  | 10/2006 | Pierce et al. |
| 2007/0087334 | A1  | 4/2007  | Dirks et al. |
| 2009/0011956 | A1  | 1/2009  | Yin et al. |
| 2009/0197271 | A1* | 8/2009  | Kotlikoff et al. ............ 435/6 |
| 2010/0021904 | A1  | 1/2010  | Pierce et al. |

FOREIGN PATENT DOCUMENTS

| EP | 0273085 | 7/1988 |
| EP | 1 479 766 A1 | 11/2004 |
| WO | WO 94/01550 | 1/1994 |
| WO | WO 99/31276 | 6/1999 |
| WO | WO 01/40516 A2 | 6/2001 |
| WO | WO 2005/098049 A2 | 10/2005 |
| WO | WO 2006/048025 A1 | 5/2006 |
| WO | WO 2007/008276 | 1/2007 |
| WO | WO 2007/044727 A2 | 4/2007 |

OTHER PUBLICATIONS

Office Action dated Feb. 4, 2010 in U.S. Appl. No. 12/152,893.
Office Action dated Apr. 1, 2010 in U.S. Appl. No. 12/467,755.
Office Action dated Apr. 16, 2010 in U.S. Appl. No. 12/454,799.
Extended European Search Report dated Apr. 22, 2010 in European Patent Application No. 06836249.0.
Final Office Action dated May 27, 2010 for U.S. Appl. No. 11/544,306.
U.S. File History printed Jun. 4, 2010 for U.S. Appl. No. 12/611,875, filed Nov. 3, 2009, entitled "Hybridization Chain Reaction,".
U.S. File History printed Jun. 4, 2010 for U.S. Appl. No. 12/395,489, filed Feb. 27, 2009, entitled "Triggered RNAi,".

(Continued)

*Primary Examiner* — Richard Schnizer
(74) *Attorney, Agent, or Firm* — Knobbe Martens Olson & Bear LLP

(57) ABSTRACT

The present application relates to methods and compositions for triggering RNAi. Triggered RNAi is highly versatile because the silencing targets are independent of the detection targets. In some embodiments, methods of silencing or modulating the expression of a marker gene are provided. The methods generally comprise providing an initiator to a cell comprising a detection target and a silencing target gene, wherein the detection target is different from the silencing target gene, wherein binding of the detection target to the initiator initiates formation of an inactivator double-stranded RNA (inactivator dsRNA). The inactivator dsRNA can silence the silencing target gene to modulate the expression of a marker gene.

30 Claims, 13 Drawing Sheets

OTHER PUBLICATIONS

U.S. File History printed Jun. 4, 2010 for U.S. Appl. No. 12/454,799, filed May 22, 2009, entitled "Compositions and Methods for Detecting Analytes,".

U.S. File History printed Jun. 4, 2010 for U.S. Appl. No. 12/467,755, May 18, 2009, entitled "Shielded Cross-Linking Probes,".

Caltech News Release, "Caltech Scientists Create New Process to Program", Sep. 6, 2010.

Final Office Action dated Sep. 20, 2010 for U.S. Appl. No. 12/454,799.

Final Office Action dated Sep. 17, 2010 for U.S. Appl. No. 12/467,755.

Schipani, Vanessa, "A targeted cancer therapy?" The Scientist, Sep. 7, 2010 blog post, http://www.the-scientist.com/blog/display/57674/.

The Naked Scientists: Science Radio & Science Podcasts, "RNA-away cancer cells", Sep. 12, 2010, http://www.thenakedscientists.com/HTML/content/news/news/2051/.

Venkataraman et al. "Selective Cell Death Mediated by Small Conditional RNAs", Proc Natl Acad Sci USA, early edition, approved Jul. 21, 2010, p. 1-6.

Venkataraman et al. Abstract of "Selective Cell Death Mediated by Small Conditional RNAs", Proc Natl Acad Sci USA, early edition, http://www.pnas.org/content/early/2010/09/01/1006377107.abstract.

Final Office Action dated Oct. 15, 2010 for U.S. Appl. No. 12/152,893.

Office Action dated Nov. 9, 2010 for U.S. Appl. No. 12/040,735.

Garcia et al., "Impact of Protein Kinase PKR in Cell Biology: from Antiviral to Antiproliferative Action." Microbiology and Molecular Biology Reviews vol. 70, No. 4 (Dec. 2006): pp. 1032-1060.

Amarzguioui et al., "Rational design and in vitro and in vitro delivery of Dicer substrate siRNA,", Nature Protocols, vol. 1, No. 2, pp. 508-517, 2006.

Bois et al., "Topological constraints in nucleic acid hybridization kinetics", Nucleic Acids Research, vol. 33, No. 13, pp. 4090-4095, 2005.

Bushnell et al., "ProbeDesigner: for the design of probesets for branched DNA (bDNA) signal amplification assays," Bioinformatics, 15(5), pp. 348-355, 1999.

Caplen, "RNAi as a gene therapy approach", Expert Opin. Biol. Ther., vol. 3, No. 4, pp. 575-586, 2003.

Check, "RNA to the rescue?", Nature, vol. 425, pp. 10-12, Sep. 4, 2003.

Coburn et al., "siRNAs: a new wave of RNA-based therapeutics", Journal of Antimicrobial Chemotherapy, vol. 51, pp. 753-756, 2003.

Coleman, R.S. and Pires, R.M. Covalent cross-linking of duplex DNA using 4-thio-2'-deoxyuridine as a readily modifiable platform for introduction of reactive functionality into oligonucleotides. Nucleic Acids Research, 1997. 25: p. 4771-4777.

Collins et al., "A branched DNA signal amplification assay for quantification of nucleic acid targets below 100 molecules/ml," Nucleic Acids Res, 25(15), pp. 2979-2984, 1997.

Coppelli et al., "Oligonucleotides as Anticancer Agents: From the Benchside to the Clinic and Beyond", Current Pharmaceutical Design, vol. 11, pp. 2825-2840, 2005.

Definition for "substantial" from Merriam-Webster Online Dictionary. Downloaded from merriam-webster.com; downloaded on Mar. 5, 2008.

Dirks et al., "Paradigms for computational nucleic acid design," Nucleic Acids Research, vol. 32, No. 4, pp. 1392-1403, Oxford University Press, 2004.

Dirks et al., "Triggered amplification by hybridization chain reaction," PNAS, vol. 101, No. 43, pp. 15275-15278, Oct. 26, 2004.

Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.

Elbashir et al., "Functional anatomy of siRNAs for mediating efficient RNAi in *Drosophila melanogaster* embryo lysate", The EMBO Journal, vol. 20, No. 23, pp. 6877-6888, 2001.

Elghanian et al.,"Selective colorimetric detection of polynucleotides based on the distance-dependent optical properties of gold nanoparticles," Science, 277(5329), pp. 1078-1081, 1997.

Ellington et al., "In vitro selection of RNA molecules that bind specific ligands," Nature 346, pp. 818-822, 1990.

Felgner, et al., "Nomenclature for Synthetic Gene Delivery Systems", Human Gene Therapy, vol. 8, pp. 511-512, Mar. 20, 1997.

Ferkol et al., "Gene Transfer into the Airway Epithelium of Animals by Targeting the Polymeric Immunoglobulin Receptor", J. Clin. Invest., vol. 95, pp. 493-502, Feb. 1995.

Ferkol et al., "Regulation of the phosphoenolpyruvate carboxykinase/human factor IX gene introduced into the lives of adult rats by receptor-mediated gene transfer", The FASEB Journal, vol. 7, pp. 1081-1091, Aug. 1993.

Fire et al., "Potent and specific genetic interference by double-stranded RNA in Caenorhabditis elegans", Nature, vol. 391, pp. 806-811, Feb. 19, 1998.

Flamm et al., "RNA folding at elementary step resolution," RNA, vol. 6, pp. 325-338, 2000.

Friedrich et al., A Cellular Screening Assay to Test the Ability of PKR to Induce Cell Death in Mammalian Cells, Molecular Therapy, vol. 12, No. 5, pp. 969-975, Nov. 2005.

Friedrich et al., "RNA molecules as anti-cancer agents", Seminars in Cancer Biology, vol. 14, pp. 223-230, 2004.

Haugland RP. The Handbook: A Guide to Fluorescent Probes and Labeling Technologies. 10th Ed. Molecular Probes/Invitrogen; 2005.

Heidel, J.D , "Targeted, systematic non-viral delivery of small interfering RNA in vivo", Doctoral thesis, California Institute of Technology, pp. 1-128, 2005.

Higuchi et al. Selective regulation of mutant K-ras mRNA expression by photo-cross-linking antisense oligonucleotide. Nucleic Acids Symposium Series (2007) vol. 51 (1) pp. 443-444.

Hofacker et al., "Fast folding and comparison of RNA secondary structures," Monatshefte für Chemie, vol. 125, pp. 167-188, 1994.

Hokaiwado et al., "RNAi-based drug discovery and its application to therapeutics", IDrugs, vol. 11, No. 4, pp. 274-278, 2008.

Hughes et al., "Double Labeling wit Fluorescence In Situ Hybridization in *Drosophila* Whole-Mount Embryos," BioTechniques, 24(4), pp. 530-532, 1998.

Huizenga et al., "A DNA Aptamer That Binds Adenosine and ATP." Biochemistry 34, pp. 656-665, 1995.

International Search Report and Written Opinion from PCT/US2005/009471, dated Mar. 8, 2006.

International Search Report and Written Opinion from PCT/US2008/055559, dated Sep. 3, 2008.

Iqbal et al., "A review of molecular recognition technologies for detection of biological threat agents", Biosensors & Bioelectronics, vol. 15, pp. 549-578, 2000.

Jagus et al., "PKR, apoptosis and cancer", The International Journal of Biochemistry & Cell Biology, vol. 31, pp. 123-138, 1999.

Jhaveri et al., "In vitro selection of signaling aptamers", Nature Biotechnology, vol. 18, pp. 1293-1297, Dec. 2000.

Judge et al., "Overcoming the Innate Immune Response to Small Interfering RNA", Human Gene Therapy, vol. 19, pp. 111-124, Feb. 2008.

Killops, K.L., Campos, L.M., Hawker, C.J. Robust, Efficient, and Orthogonal Synthesis of Dendrimers via Thiol-ene "Click" Chemistry. Journal of the American Chemical Society, 2008. 130: p. 5062-5064.

Kim et al., "Synthetic dsRNA Dicer substrates enhance RNAi potency and efficacy", Nature Biotechnology, vol. 23, No. 2, pp. 222-226, Feb. 2005.

Kislauskis et al. "Isoform-specific 3'-untranslated Sequences Sort α-cardiac and β-cytoplasmic Actin Mesenger RNAs to Different ytoplasmic Compartments," The Journal of Cell Biology, 123(1), pp. 165-172, 1993.

Kosman, et al., "Multiplex Detection of RNA Expression in *Drosophila* Embryos," Science, 305, p. 846, 2004.

Ladiges, et al., "Tissue specific expression of PKR protein kinase in aging B6D2F1 mice," Mechanisms of Ageing and Development, vol. 114, pp. 123-132, (2000).

Lawrence et al., "Highly Localized Tracks of Specific Transcripts within Interphase Nuclei Visualized by In Situ Hybridication," Cell, 57, pp. 493-502, 1989.

Levsky et al., "Single-Cell Gene Expression Profiling," Science 297, pp. 836-840, 2002.

Liu et al., "A colorimetric lead biosensor using DNAzyme-directed assembly of gold nanoparticles," J. Am. Chem. Soc., 125(22), pp. 6642-6643, 2003.

Macechko et al., "Comparison of Immunologic Amplification vs Enzymatic Deposition of Fluorochrome-conjugated Tyramide as Detection Systems for FISH," J Histochem Cytochem, 45(3), pp. 359-363, 1997.

Mahato et al., "Modulation of gene expression by antisense and antigene oligodeoxynucleotides and small interfering RNA", Expert Opin. Drug Deliv., vol. 2, No. 1, pp. 3-28. 2005.

Manche et al., "Interactions between Double-Stranded RNA Regulators and the Protein Kinase DAI", Molecular and Cellular Biology, vol. 12, No. 11, pp. 5238-5248, Nov. 1992.

Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807, 2001.

Mittelstadt, et al., "Interaction of human tRNA-dihydrouridine synthase-2 with interferon-induced protein kinase PKR," Nucleic Acids Research, vol. 36, No. 3, pp. 998-1008, (2008).

Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292, American Chemical Society, 2002.

Nutiu et al., "Structure-switching signaling aptamers," J. Am. Chem. Soc., vol. 125, pp. 4771-4778, American Chemical Society, 2003.

Opalinska et al., "Nucleic-Acid Therapeutics: Basic Principles and Recent Applications", Nature Reviews Drug Discovery, vol. 1, pp. 503-514, 2002.

Park et al., "Rapid Identification of *Candida dubliniensis* Using a Species-Specific Molecular Beacon", Journal of Clinical Microbiology, vol. 38, No. 8, pp. 2829-2836, 2000.

Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.

Pieles, U. and Englisch, U. Psoralen covalently linked to oligodeoxyribonucleotides: synthesis, sequence specific recognition of DNA and photo-cross-linking to purimidine residues of DNA. Nucleic Acids Research, 1989. 17: p. 285-299.

Player et al., "Single-copy Gene Detection Using Branched DNA (bDNA)) In Situ Hybridization," J. Histochem & Cytochem, 49(5), pp. 603-611, 2001.

Pouton et al., "Key issues in non-viral gene delivery", Advanced Drug Delivery Reviews, vol. 46, pp. 187-203, 2001.

Qian et al., "Recent Developments in Signal Amplification Methods for In Situ Hybridization," Diagnostic Molecular Pathology, 12(1), pp. 1-13, 2003.

Qian, X., L. Jin, and R.V. Lloyd, In situ hybridization: basic approaches and recent development. The Journal of Histotechnology, 2004. 27(1): p. 53-67.

Rachofsky et al., "Probing structure and dynamics of DNA with 2-aminopurine: Effects of local environment on fluorescence," Biochemistry, vol. 40, pp. 946-956, 2001.

Read et al., "Barriers to Gene Delivery Using Synthetic Vectors", Advances in Genetics, vol. 53, pp. 19-46, 2005.

Scherer et al., "Approaches for the sequence-specific knockdown of mRNA", Nature Biotechnology, vol. 21, No. 12, pp. 1457-1465, 2003.

Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.

Schweitzer et al., "Combining nucleic acid amplification and detection," Curr Opin Biotechnol, 12, pp. 21-27, 2001.

Seelig et al., "Catalyzed Relaxation of a Metastable DNA Fuel", Journal American Chemical Society, vol. 128, No. 37, pp. 12211-12220, 2006.

Seeman, "Nucleic acid junctions and lattices," J. Theor. Biol., vol. 99, pp. 237-247, Academic Press Inc. (London) Ltd., 1982.

Shir et al., "Inhibition of glioma growth by tumor-specific activation of double-stranded RNA-dependent protein kinase PKR", Nature Biotechnology, vol. 20, pp. 895-900, Sep. 2002.

Sokol et al., "Real time detection of DNA•RNA hybridization in living cells", Proc. Natl. Acad. Sci. USA, vol. 95, pp. 11538-11543, Sep. 1998.

Storhoff et al., "One-pot colorimetric differentiation of polynucleotides with single base imperfections using gold nanoparticles," J. Am. Chem. Soc., 120, pp. 1959-1964, 1998.

Supplementary European Search Report from PCT/US2005/009471, dated May 6, 2008.

Tijsterman et al., "Dicers at RISC: The Mechanism of RNAi", Cell, vol. 117, pp. 1-3, 2004.

Tuerk et al., "Systematic Evolution of Ligands by Exponential Enrichment: RNA Ligands to Bacteriophage T4 DNA Polymerase," Science 249, pp. 505-510, 1990.

Turberfield, et al., "DNA fuel for free-running nanomachines,"Physical Review Letters, vol. 90, No. 11, pp. 118102-1-118102-4, Mar. 21, 2003.

Tyagi et al., "Molecular Beacons: Probes that Fluoresce upon Hybridization," Nature Biotechnology 14, pp. 303-308, 1996.

U.S. File History printed Jun. 16, 2009 for U.S. Appl. No. 11/087,937, filed Mar. 22, 2005, entitled "Hybridization Chain Reaction,".

U.S. File History printed Jun. 16, 2009 for U.S. Appl. No. 11/371,346, filed Mar. 7, 2006, entitled "Hybridization Chain Reaction Amplification for In Situ Imaging,".

U.S. File History printed Jun. 16, 2009 for U.S. Appl. No. 11/371,347, filed Mar. 7, 2006, entitled "Colorimetric Readout of Hybridization Chain Reaction,".

U.S. File History printed Jun. 16, 2009 for U.S. Appl. No. 11/544306, filed Oct. 6, 2006, entitled "PKR Activation Via Hybridization Chain Reaction,".

U.S. File History printed Jun. 16, 2009 for U.S. Appl. No. 12/040735, Feb. 29, 2008, entitled "Triggered RNAi,".

U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways,".

Van De Corput et al., "Sensitive mRNA Detection by Fluorescence In Situ Hybridization Using Horseradish Peroxidase-labeled Oligodeoxynucleotides and Tyramide Signal Amplification," J. Histochem Cytochem, 46(11), pp. 1249-1259, 1998.

Vermeulen et al., "The contributions of dsRNA structure to Dicer specificity and efficiency", RNA, vol. 11, pp. 674-682, 2005.

Volker, et al., "Conformational energetics of stable and metastable states formed by DNA triple repeat oligonucleotides: implications for triplet expansion diseases,"PNAS, vol. 99, No. 23, pp. 14700-14705, Nov. 12, 2002.

Wagner et al., "Transferrin-Polycation Conjugates as Carriers for DNA Uptake into Cells", Proceedings of the National Academy of Sciences of the United States of America, vol. 87, pp. 3410-3414, May 1990.

Wilkie et al., "Transcribed genes are localized according to chromosomal position within polarized *Drosophila* embryonic nuclei," Current Biology, 9, pp. 1263-1266, 1999.

Williams, B.R.G., "PKR; a sentinel kinase for cellular stress", Oncogene, vol. 18, pp. 6112-6120, 1999.

Willis, M.C., et al. Photocross-linking of 5-Iodouracil-Substituted RNA and DNA to Proteins. Science, 1993. 262: p. 1255-1257.

Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.

Wu et al., "Receptor-mediated in Vitro Gene Transformation by a Soluble DNA Carrier System", The Journal of Biological Chemistry, vol. 262, No. 10, pp. 4429-4432, 1987.

Yin et al., "Programming biomolecular self-assembly pathways", Nature, vol. 451, pp. 318-323, Jan. 17, 2008.

Zhang et al., Targeted Gene Silencing by Small Interfering RNA-Based Knock-Down Technology, Current Pharmaceutical Biotechnology, vol. 5, pp. 1-7, 2004.

Zheng et al., "Activation of the protein kinase PKR by short double-stranded RNAs with single-stranded tails", RNA, vol. 10, pp. 1934-1945, 2004.

Zhou et al., "RNA Interference and Potential Applications", Current Topics in Medicinal Chemistry, vol. 6, pp. 901-911, 2006.

Zuker et al., "Optimal computer folding of large RNA sequence using thermodynamics and auxiliary information," Nucleic Acids Research, vol. 9, No. 1, pp. 133-147, 1981.

Aagaard et al., "RNAi Therapeutics: Principles, Prospects and Challenges." *Advanced Drug Delivery Reviews* 59 (2007): 75-86.

Castanotto et al., "The Promises and Pitfalls of RNA-Interface-Based Therapeutics." *Nature* 457 (Jan. 22, 2009):426-433.

Final Office Action dated Jul. 15, 2011, received in U.S. Appl. No. 12/040,735.

Final Office Action dated Jul. 25, 2011, received in U.S. Appl. No. 12/395,489.

Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." *Cancer Research* 65.19 (Oct. 1, 2005): 8984-8992.

Takei et al., "A Small Interfering RNA Targeting Vascular Endothelial Growth Factor as Cancer Therapeutics." *Cancer Research* 64. (May 15, 2004): 3365-3370.

"These Cells Will Self-Destruct in Five . . . Four . . . ," National Science Foundation, Sep. 6, 2010, printed Sep. 16, 2010, Press Release 10-160, pp. 1-3. (http://www.nsf.gov/news/news_summ.jsp?cntn_id=117641&org=CISE&from=news).

Office Action dated Dec. 16, 2010 for U.S. Appl. No. 12/395,489.

Office Action dated Mar. 17, 2011 for U.S. Appl. No. 12/611,875.

Extended European Search Report dated Nov. 7, 2011 in Application No. 08755764.1, filed May 16, 2008.

Seeman, N.C., "DNA in a material world" *Nature*, vol. 421, No. 23, Jan. 23, 2003, pp. 427-431.

Seeman, N.C., "Nucleic Acid Nanostructures and Topology" *Angew. Chem. Int. Ed.*, vol. 37, 1998, pp. 3220-3238.

Yurke, et al., "A DNA-fuelled molecular machine made of DNA" *Nature*, vol. 406, Aug. 10, 2000, pp. 605-608.

Allan et al., "A Concise Total Synthesis of (−)-Quinocarcin via Aryne Annulation." *Journal of American Chemical Society* 130 (2008) 17270-17271.

Behenna et al., "The Enantioselective Tsuji Allylation." *Journal of American Chemical Society* 126.46 (2004): 15044-15045.

Bloomfield et al., "Nucleic Acids: Structures, Properties, and Functions." *University Science Books* (2000).

Bolt et al., Differential Reactivities of the mono- and di-epoxide of 1,3-butadiene. *Toxicology* 113 (1996): 294-296.

Bumcrot et al., "RNAi Therapeutics: A Potential New Class of Pharmaceutical Drugs." *Nature Chemical Biology* 2.12 (Dec. 2006): 711-719.

Cerutti et al., "On the Origin and Functions of RNA-Mediated Silencing: From Protists to Man." *Current Genetics* 50 (2006) 81-99.

Coleman et al., "Template-Directed Cross-Linking of Oligonucleotides: Site-Specific Covalent Modification of dG-N7 Within Duplex DNA." J. Org. Chem. 60 (1995): 6252-6253.

Cullen et al., "Genome-wide Screening for Gene Function Using RNAi in Mammalian Cells." *Immunology and Cell Biology* 83 (2005) 217-223.

Czauderna et al., "Structural Variations and Stabilising Modifications of Synthetic siRNAs in Mammalian Cells." *Nucleic Acids Research* 31.11 (2003): 2705-2716.

Dias et al., "Antisense Oligonucleotides: Basic Concepts and Mechanisms." *Molecular Cancer Therapeutics* 1 (Mar. 2002) 347-355.

Dirks et al., "A Partition Function Algorithm for Nucleic Acid Secondary Structure Including Pseudoknots." *Journal of Computational Chemistry* 24.13 (2003) 1664-1677.

Dirks et al., "An Algorithm for Computing Nucleic Acid Base-Pairing Probabilities Including Pseudoknots." *Journal of Computational Chemistry* 25.10 (2004): 1295-1304.

Dirks et al., "Thermodynamic Analysis of Interacting Nucleic Acid Strands." *SIAM Review* 49.1 (2007): 65-88.

Elmén et al., "Locked Nucleic Acid (LNA) Mediated Improvements in siRNA Stability and Functionality." *Nucleic Acids Research* 33.1 (2005): 439-447.

Enquist et al.., "The Total Synthesis of (+)- Cyanthiwigin F by Means of Double Catalytic Enantioselective Alkylation." *Nature* 453.7199 (Jun. 26, 2008) 1228-1231.

Femino et al., "Visualization of Single Molecules of mRNA in Situ" *Methods of Enzymology* 361 (2003): 245-304.

Ferreira et al., "The Palladium-Catalyzed Oxidative Kinetic Resolution of Secondary Alcohols with Molecular Oxygen." *Journal of American Chemical Society* 123.31 (2001): 7725-7726.

Final Office Action dated Jul. 15, 2011 for U.S. Appl. No. 12/040,735.

Final Office Action dated Jul. 25, 2011 for U.S. Appl. No. 12/395,489.

Garg et al., "A Ligand-free Solid-supported System for Sonogashira Couplings: Applications in Nucleoside Chemistry." *Chem. Commun.* (2005) 4551-4553.

Garg et al., "Development of an Enantiodivergent Strategy for the Total Synthesis of (+)- and (−)- Dragmacidin F from a Single Enantiomer of Quinic Acid." *Journal of American Chemical Society* 127 (2005) 5970-5978.

Gilman et al., "The Biological Actions and Therapeutic Applications of the B-Chloroethyl Amines and Sulfides." *Science* 103.2675 (Apr. 5, 1946): 409-415.

Hashimoto et al., "Recent Progress in Diazirine-Based Photoaffinity Labeling." *Eur. J. Org. Chem.* (2008): 2513-2523.

Hearst et al., "Psoralen Photochemistry." *Ann.Rev. Biophys.Bioeng.* 10 (1981): 69-86.

Herath et al., "Synthesis of Acrimarins from 1,3,5-Trioxygenated-9-acridone Derivatives." *Journal of Heterocyclic Chem.* 41 (2004): 23-28.

Judge et al., "Design of Noninflammatory Synthetic siRNA Mediating Potent Gene Silencing in Vivo." *Molecular Therapy* 13.3 (Mar. 2006): 494-505.

Julian et al., "Biomimetic Approaches to Gas Phase Peptide Chemistry: Combining Selective Binding Motifs with Reactive Carbene Precursors to Form Molecular Mousetraps." *International Journal of Mass Spectrometry* 228 (2003): 851-864.

Julian et al., "Molecular Mousetraps: Gas-Phase Studies of the Covalent Coupling of Noncovalent Complexes Initiated by Reactive Carbenes Formed by Controlled Activation of Diazo Precursors." *Agnew. Chem.Int. Ed.* 42.9 (2003) 1012-1015.

Kadnikov et al., "Synthesis of Coumarins via Palladium—Catalyzed Carbonylative Annulation of Internal Alkynes by o-Iodophenols." *Organic Letters* 2.23 (2000): 3643-3646.

Kim et al., "Strategies for Silencing Human Disease Using RNA Interference." *Nature Review Genetics* 8 (Mar. 2007) 173-184.

Knorre et al., "Photoaffinity Labeling as an Approach to Study Supramolecular Nucleoprotein Complexes." *FEBS Letters* 433 (1998): 9-14.

Kobertz et al., "An Efficient Synthesis of a Furan-Side Furocoumarin Thymidine Monoadduct." *J. Org. Chem.* 62.8 (1997) 2630-2632.

Kobertz et al., "Solid-Phase Synthesis of Oligonucleotides Containing a Site-Specific Psoralen Derivative." *Journal of American Chemical Society* 119 (1997): 5960-5961.

Kobertz et al., "Total Synthesis of a Cis-Syn 2-Carbomethoxypsoralen Furan-Side Thymidine Monoadduct." *Journal of American Chemical Society* 118 (1996): 7101-7107.

Lacenere et al., "Effects of a Modified Dye-Labeled Nucleotide Spacer Arm on Incorporation by Thermophilic DNA Polymerases." *Nucleosides, Nucleotides, and Nucleic Acids* 25 (2006) 9-15.

Lawley et al., "DNA Adducts from Chemotherapeutic Agents." *Mutation Research—Fundamental and Molecular mechanisms of Mutagenesis* 355 (1996): 13-40.

Layzer et al., "In Vivo Activity of Nuclease-Resistant siRNAs." *RNA* 10 (2004): 766-771.

Manoharan et al., "RNA Interference and Chemically Modified Small Interfering RNAs." *Current Opinion in Chemical Biology* 8 (2004): 570-579.

Meinhardt et al., "Wavelength-dependent Penetration Depths of Ultraviolet Radiation in Human Skin." Journal of Biomedical Optics 13.4 (Jul./Aug. 2008) 044030-1-044030-5.

Mohr et al., "Catalytic Enantioselective Decarboxylative Protonation." *Journal of American Chemical Society* 128.35 (2006): 11348-11349.

Mohr et al., "Natural Products as Inspiration for the Development of Asymmetric Catalysis." *Nature* 455 (Sep. 18, 2008) 323-332.

Noll et al., "Preparation of Interstrand Cross-Linked DNA Oligonucleotide Duplexes." *Frontiers in Bioscience* 9 (Jan. 1, 2004): 421-437.

Noll et al., "Formation and Repair of Interstrand Cross-Links in DNA." *Chemical Reviews* 106.2 (2006) 277-301.

Raj et al., "Imaging Individual mRNA Molecules Using Multiple Singly Labeled Probes." *Nature Methods* 5.10 (Oct. 2008): 877-879.

Reynolds et al., "Rational siRNA Design for RNA Interference." *Nature Biotechnology* 22.3 (Mar. 2004) 326-330.

Saunders et al., "Introduction of DNA into Bacteria." *Methods in Microbiology* 29 (1999): 3-49.

Schärer et al., "DNA Interstrand Crosslinks: Natural and Drug-Induced DNA Adducts that Induce Unique Cellular Responses." *ChemBioChem* 6 (2005): 27-32.

Schulte-Merker et al., "no tail (ntl) is the zebrafish homologue of the mouse T (Brachyury) gene." *Development* 120 (1994): 1009-1015.

Shah et al., "The Fries Isomerization of Acetyl and Benzoyl Esters of Umbelliferones." *J. Org. Chem.* 19 (1954): 1681-1685.

Silverman et al., "Quenched Autoligation Probes Allow Discrimination of Live Bacterial Species by Single Nucleotide Differences in rRNA." *Nucleic Acids Research* 33.15 (2005): 4978-4986.

Silverman et al., "Oligonucleotide Probes for RNA-Targeted Fluorescence In Situ Hybridization." *Advances in Clinical Chemistry* 43 (2007): 79-115.

Siolas et al., "Synthetic shRNAs as Potent RNAi Triggers." *Nature Biotechnology* 23.2 (Feb. 2005): 227-231.

Sun et al., "Side Chain Chemistry Mediates Backbone Fragmentation in Hydrogen Deficient Peptide Radicals." *Journal of Proteome Research* 8 (2009) 958-966.

Tani et al., "Synthesis and Structural Analysis of 2-Quinuclidonium Tetrafluoroborate." *Nature* 441 (Jun. 8, 2006) 731-734.

Thomas et al., "Photoaffinity Cross-Linking and RNA Structure Analysis." *Methods in Enzymology* 318 (2000) 136-147.

Venkataraman et al., "An Autonomous Polymerization Motor Powered by DNA Hybridization." *Nature Nanotechnology* 2 (Aug. 2007): 490-494.

Vodovozova et al., "Photoaffinity Labeling and Its Application in Structural Biology." *Biochemistry* (Moscow) 72.1 (2007): 1-20.

Voorhoeve et al., "Knockdown Stands Up.:" *Trends in Biotechnology* 21.1 (Jan. 2003) 2-4.

Wassarman et al., "Psoralen Crosslinking of Small RNAs in vitro." *Molecular Biology Reports* 17 (1993): 143-151.

White et al., "The Catalytic Asymmetric Total Synthesis of Elatol." *Journal of American Chemical Society* 130.3 (2008): 810-811.

Wijen et al., "The in vivo Genetic Activity Profile of the Monofunctional Nitrogen Mustard 2-Chloroethylamine Differs Drastically from its Bifunctional Counterpart Mechlorethamine." *Carcinogenesis* 21.10 (2000) 1859-1867.

Yoshimura et al., "Interstrand Photocrosslinking of DNA via p-carbamoylvinyl Phenol Nucleoside." *Bioorganic & Medicinal Chemistry Letters* 15 (2005): 1299-1301.

\* cited by examiner

FIG. 3A
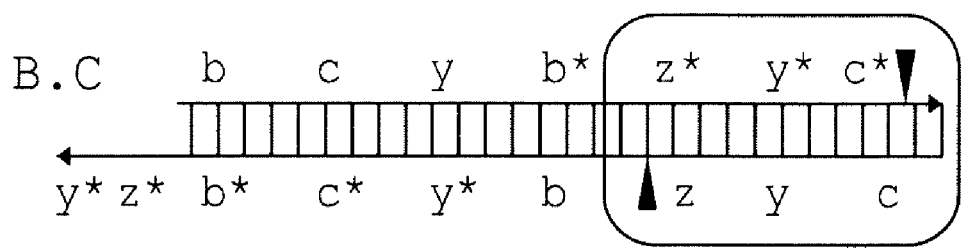
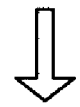
Dicer/RNAi action
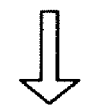
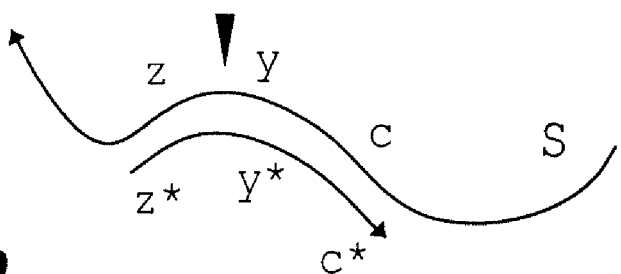
FIG. 3B

US 8,241,854 B2

TRIGGERED RNAI

CROSS-REFERENCE TO RELATED APPLICATIONS

The present application claims priority to U.S. Provisional Application No. 61/128,550, filed May 22, 2008, which is hereby incorporated by reference in its entirety.

STATEMENT REGARDING FEDERALLY SPONSORED R&D

This invention was made with government support under grant nos. NIH 5R01EB006192-04 "Hybridization chain reaction: in situ amplification for biological imaging" and NIH P50 HG004071 "Center for in toto genomic analysis of vertebrate development".

BACKGROUND OF THE INVENTION

1. Field of the Invention

The present application relates generally to nucleic acid systems for triggering RNAi for modulating the expression of one or more marker genes in the presence of a detection target.

2. Description of the Related Art

RNA interference (RNAi) is a conserved biological response to double-stranded RNA (dsRNA) that results in sequence-specific silencing of target gene expression (Fire et al. 1998 Nature* 391: 806-811). In recent years, RNAi has been adopted as an important experimental tool to study and manipulate gene expression and has generated great interest as a potential therapeutic approach (Dillon et al. 2005 *Annual Review of Physiology* 67: 147-173, incorporated herein by reference in its entirety).

Until now, in the practice of using RNAi for gene silencing, an RNA duplex is introduced into the cell cytoplasm such that one of the strands in the duplex matches the sequence of the target mRNA to be silenced. In the traditional RNAi pathway, an "inactivator dsRNA" is introduced into the cell's cytoplasm and is processed by the Dicer enzyme, producing small interfering RNAs (siRNAs). (See, Tijsterman and Plasterk 2004 *Cell* 117(1): 1-3, incorporated herein by reference in its entirety). The siRNAs are then processed by the RNA-induced silencing complex (RISC complex), which unwinds the siRNA and retains one strand as a targeting co-factor. The RISC-siRNA complex recognizes and induces the degradation of the target mRNA, which is complementary to the siRNA strand retained by the RISC complex. The cleaved mRNA is then further degraded by natural mechanisms. The traditional RNAi mechanism implements the logical operation: if gene q is detected, silence gene q. Thus, using the standard RNAi technique, the detection and silencing steps are restricted to operating on the same gene.

SUMMARY OF THE INVENTION

In some embodiments, methods of detecting the presence of a detection target by modulating the expression of a marker gene are provided. In some embodiments, the methods generally comprise providing an initiator to a cell comprising a detection target, a silencing target gene, and a marker gene, wherein the detection target is different from the silencing target gene; providing a first substrate monomer to the cell, wherein the first substrate monomer comprises a silencing target complement region that is substantially complementary to a portion of the silencing target gene, and an initiator complement region that is substantially complementary to a portion of the initiator; and providing a second substrate monomer to the cell, wherein the second substrate monomer comprises a silencing target region that is substantially complementary to the silencing target complement region, wherein binding of the detection target to the initiator initiates formation of an inactivator double-stranded RNA (inactivator dsRNA) which silences the silencing target gene, and wherein said silencing of the silencing target gene modulates the expression of said marker gene; determining the level of expression of said marker gene; and assessing whether said maker gene is expressed at a level that is different than a predetermined level, thereby detecting the presence of said detection target.

In further embodiments, methods of detecting the presence of a detection target by modulating the expression of a marker gene generally comprise contacting a cell comprising a detection target, a silencing target gene, and a marker gene with an initiator comprising a detection target binding region and an initiator region, wherein the detection target binding region can interact with the detection target, and wherein the detection target is different from the silencing target gene; contacting the cell with a first substrate monomer, wherein the first substrate monomer comprises a silencing target complement region and an initiator complement region that is complementary to the initiator region of the initiator monomer, wherein upon binding of the detection target region to a detection target, the initiator region of the initiator is made available to bind to the initiator complement region of the first substrate monomer; and contacting the cell with a second substrate monomer, wherein the second substrate monomer comprises an silencing target region that is complementary to the silencing target complement region of the first substrate monomer, wherein upon binding of the initiator complement region to the initiator region, the silencing target complement region of the first substrate monomer is made available to bind to the silencing target region of the second substrate monomer, wherein an inactivator double-stranded RNA (inactivator dsRNA) is formed by hybridization of the silencing target complement region to the silencing target region, wherein the inactivator dsRNA is processed to silence the silencing target gene, and wherein said silencing of the silencing target gene modulates the expression of said marker gene; determining the level of expression of said marker gene; and assessing whether said maker gene is expressed at a level that is different than a predetermined level, thereby detecting the presence of said detection target.

In additional embodiments, methods of detecting the presence of a detection target by modulating the expression of a marker gene generally comprise contacting a cell comprising a detection target, a silencing target gene, and a marker gene with an initiator comprising a detection target binding region, an initiator region, and a silencing target complement region wherein the detection target binding region can interact with the detection target, and wherein the detection target is different from the silencing target gene; and contacting the cell with a substrate monomer, wherein the substrate monomer comprises an initiator complement region that is complementary to the initiator region of the RNA hairpin initiator monomer and a silencing target region that is complementary to the silencing target complement region, wherein an inactivator double-stranded RNA (inactivator dsRNA) is formed by hybridization of the silencing target complement region to the silencing target region subsequent to interaction of the detection target to the detection target binding region, wherein the inactivator dsRNA silences the silencing target gene, and wherein said silencing of the silencing target gene modulates the expression of said marker gene; determining the level of expression of said marker gene; and assessing whether said maker gene is expressed at a level that is different than a predetermined level, thereby detecting the presence of said detection target.

In some embodiments, methods of detecting the presence of a detection target by modulating the expression of a marker gene generally comprise contacting a cell comprising a detection target, a silencing target gene, and a marker gene with an initiator comprising a detection target binding region and an initiator region, wherein the detection target binding region can interact with the detection target, and wherein the detection target is different from the silencing target gene; contacting the cell with a first substrate monomer and a second substrate monomer: wherein the first substrate monomer comprises a second substrate monomer complement region and the second substrate monomer comprises a first substrate monomer complement region, wherein the second substrate monomer complement region is complementary to the first substrate monomer complement region; wherein the first substrate monomer comprises a silencing target complement region and an initiator complement region that is complementary to the initiator region of the initiator, wherein upon binding of the detection target binding region to the detection target, the initiator region of the initiator is made available to bind to the initiator complement region of the first substrate monomer; wherein the second substrate monomer comprises a silencing target region that is complementary to the silencing target complement region of the first substrate monomer, wherein upon binding of the initiator complement region of the first monomer to the initiator region of the initiator, the silencing target complement region of the first substrate monomer hybridizes to the silencing target region of the second substrate monomer to form an inactivator dsRNA, wherein the inactivator dsRNA is processed to silence the silencing targeting gene, and wherein said silencing of the silencing target gene modulates the expression of said marker gene; determining the level of expression of said marker gene; and assessing whether said maker gene is expressed at a level that is different than a predetermined level, thereby detecting the presence of said detection target. In some embodiments, the initiator comprises a nucleic acid hairpin monomer. In some embodiments, the first substrate monomer comprises a nucleic acid hairpin monomer that comprises a first hairpin loop region. In some embodiments, the first hairpin loop region comprises the second substrate monomer complement region. In some embodiments, the second substrate monomer comprises a nucleic acid hairpin monomer that comprises a second hairpin loop region. In some embodiments, the second hairpin loop region comprises the first substrate monomer complement region. In some embodiments, the silencing target gene comprises said marker gene. In some embodiments, the silencing target gene comprises a nucleic acid sequence that modulates the expression of said marker gene. In some embodiments, the marker gene is GFP. In some embodiments, the first substrate monomer comprises a sticky end region.

In further embodiments, methods of detecting the presence of a detection target by modulating the expression of a marker gene generally comprise contacting a cell comprising a detection target, a silencing target gene, and a marker gene with an initiator comprising a detection target binding region and an initiator region, wherein the detection target binding region can interact with the detection target, and wherein the detection target is different from the silencing target gene; contacting the cell with a first substrate complex and a second substrate complex: wherein the first substrate complex comprises a second substrate complex complement region and the second substrate complex comprises a first substrate complex complement region, wherein the second substrate complex complement region is complementary to the first substrate complex complement region; wherein the first substrate complex comprises a silencing target region and an initiator complement region that is complementary to the initiator region of the initiator, wherein upon binding of the detection target binding region of the initiator to the detection target, the initiator region of the initiator is made available to bind to the initiator complement region of the first substrate complex; and wherein the second substrate complex comprises a silencing target complement region, wherein upon binding of the initiator complement region to the initiator region, the silencing target region of the first substrate complex is made available to bind to the silencing target complement region of the second substrate complex; wherein an inactivator double-stranded RNA (inactivator dsRNA) is formed by hybridization of the silencing target complement region to the silencing target region, and wherein the inactivator dsRNA is processed to silence the silencing target gene, and wherein said silencing of the silencing target gene modulates the expression of said marker gene; determining the level of expression of said marker gene; and assessing whether said maker gene is expressed at a level that is different than a predetermined level, thereby detecting the presence of said detection target. In some embodiments, the first substrate complex comprises a nucleic acid duplex. In some embodiments, the second substrate complex comprises a nucleic acid duplex. In some embodiments, the first substrate complex comprises a region complementary to a region of the second substrate complex. In some embodiments, the first substrate complex comprises a first bulge loop region. In some embodiments, the second substrate complex comprises a second bulge loop region, wherein a portion of the first bulge loop region is complementary to the second bulge loop region. In some embodiments, the silencing target gene comprises said marker gene. In some embodiments, the silencing target gene comprises a nucleic acid sequence that modulates the expression of said marker gene. In some embodiments, the marker gene is GFP.

In some embodiments, methods of detecting the presence of a detection target by modulating the expression of a marker gene generally comprise contacting a cell comprising a detection target gene, a silencing target gene, and a marker gene with an initiator comprising a detection target binding region and an initiator region, wherein the detection target binding region interacts with the detection target, and wherein the detection target is different from the silencing target gene; contacting the cell with a first substrate complex and a second substrate complex: wherein the first substrate complex comprises a silencing target complement region and an initiator complement region that is complementary to the initiator region of the initiator, wherein upon binding of the detection target binding region of the initiator to the detection target, the initiator region of the initiator binds to the initiator complement region of the first substrate complex; and wherein the second substrate complex comprises a silencing target region, wherein upon binding of the initiator complement region to the initiator region, the silencing target region of the second substrate complex binds to the silencing target complement region of the first substrate complex; wherein an inactivator dsRNA is formed by hybridization of the silencing target complement region to the silencing target region, wherein the inactivator dsRNA is processed to silence the silencing target gene, and wherein said silencing of the silencing target gene modulates the expression of said marker gene; determining the level of expression of said marker gene; and assessing whether said maker gene is expressed at a level that is different than a predetermined level, thereby detecting the presence of said detection target. In some embodiments, the first substrate complex comprises a nucleic acid duplex. In some embodiments, the second substrate complex comprises a nucleic acid duplex. In some embodiments, the silencing target gene comprises said marker gene. In some embodiments, the silencing target gene comprises a nucleic acid sequence that modulates the expression of said marker gene. In some embodiments, the marker gene is GFP.

In some embodiments, methods of detecting the presence of a detection target by modulating the expression of a marker gene generally comprise contacting a cell comprising a detection target, a silencing target gene, and a marker gene with an initiator comprising a detection target binding region, an initiator region, and a silencing target complement region wherein the detection target binding region can interact with the detection target, and wherein the detection target is different from the silencing target gene; and contacting the cell with a substrate monomer: wherein the substrate monomer comprises an initiator complement region that is complementary to the initiator region of the RNA hairpin initiator monomer and a silencing target region that is complementary to the silencing target complement region; wherein the initiator and substrate monomer co-exist stably in the absence of a detection target; and wherein an inactivator double-stranded RNA (inactivator dsRNA) is formed by hybridization of the silencing target complement region to the silencing target region subsequent to interaction of the detection target to the detection target binding region, wherein the inactivator dsRNA silences the silencing target gene, and wherein said silencing of the silencing target gene modulates the expression of said marker gene; determining the level of expression of said marker gene; and assessing whether said maker gene is expressed at a level that is different than a predetermined level, thereby detecting the presence of said detection target. In some embodiments, the silencing target gene comprises said marker gene. In some embodiments, the silencing target gene comprises a nucleic acid sequence that modulates the expression of said marker gene. In some embodiments, the marker gene is GFP.

In some embodiments, upon binding of the detection target to the initiator, a portion of the initiator is made available to bind to the initiator complement region of the first substrate monomer.

In some embodiments, upon binding of the initiator complement region to the initiator, the silencing target complement region is made available to bind to the silencing target region of the first substrate monomer.

In some embodiments, upon binding of the silencing target region to the silencing target complement region, the inactivator dsRNA is formed.

In some embodiments, the initiator comprises a nucleic acid hairpin monomer, such as an RNA hairpin monomer. In some embodiments, the initiator comprises a conformation-switching aptamer.

In some embodiments, one or more monomers (e.g., the first substrate monomer and/or the second substrate monomer) are nucleic acid hairpin monomers, such as an RNA hairpins. In some embodiments, one or more monomers can comprise sticky ends.

In some embodiments, the methods further comprise contacting the cell with at least one accessory molecule comprising a nucleic acid sequence that binds to a region flanking the initiator binding site of the detection target.

In some embodiments, the initiator region is able to bind to the initiator complement region when a detection target is present in the cell.

In some embodiments, the inactivator dsRNA can be processed by Dicer. In some embodiments, the inactivator dsRNA can be processed to produce a 19 bp duplex with 2-nt 3' overhangs. In some embodiments, the inactivator dsRNA comprises a RNA duplex substrate from about 19 bp in length to about 22 bp in length. In some embodiments, the inactivator dsRNA is an siRNA. In some embodiments, the inactivator dsRNA is a 19 bp duplex with 2-nt 3' overhangs.

In some embodiments, the silencing target gene is an mRNA comprising a sequence different from the sequence of the detection target.

In some embodiments, the detection target is associated with a disease or disorder. In some embodiments, the detection target is a nucleic acid. In some embodiments, the detection target is an mRNA associated with a cancer. In some embodiments, the detection target is a viral nucleic acid. In some embodiments, the detection target is an mRNA molecule associated with a disease or disorder.

In some embodiments, the silencing target gene is an mRNA (e.g., an mRNA of a marker or reporter gene). In some embodiments, the silencing target gene comprises said marker gene. In some embodiments, the silencing target gene comprises a nucleic acid sequence that modulates the expression of said marker gene. In some embodiments, the marker gene encodes GFP.

In some embodiments, the initiator comprises a recognition molecule such that upon binding of the recognition molecule to the detection target, a portion of the initiator is made available to bind to the initiator complement region of the first substrate monomer. In some embodiments, the recognition molecule is an aptamer.

In some embodiments, the detection target is a nucleic acid. In some embodiments, the detection target is selected from the group consisting of polypeptides, carbohydrates, lipids and small molecules.

In some embodiments, the methods are conducted in vitro. In some embodiments, the methods are conducted in vivo.

In some embodiments, methods of diagnosing a disease or disorder are provided. In some embodiments, the methods generally comprise providing an initiator to a cell comprising a detection target, a silencing target gene, and a marker gene, wherein the detection target is a nucleic acid associated with the disease or disorder, and the silencing target gene is different from the detection target; providing a first substrate monomer to the cell, wherein the first substrate monomer comprises a silencing target complement region and an initiator complement region that is substantially complementary to a portion of initiator monomer; and providing a second substrate monomer to the cell, wherein the second substrate monomer comprises a silencing target region that is substantially complementary to the silencing target complement region, wherein the initiator and the first substrate monomer hybridize in the presence of the detection target to form an inactivator double-stranded RNA (inactivator dsRNA) which silences the silencing target gene, and wherein said silencing of the silencing target gene modulates the expression of said marker gene; determining the level of expression of said marker gene; and assessing whether said maker gene is expressed at a level that is different than a predetermined level, thereby diagnosing the disease or disorder.

In some embodiments, kits for detecting the presence of a detection target by modulating the expression of a marker gene are provided. In some embodiments, the kits generally comprise an initiator comprising a detection target binding region and an initiator region; a first substrate monomer, wherein the first substrate monomer comprises a silencing target complement region and an initiator complement region that is complementary to the initiator region of the initiator monomer; a second substrate monomer, wherein the second substrate monomer comprises a silencing target region that is complementary to the silencing target complement region of the first substrate monomer; and a marker gene.

BRIEF DESCRIPTION OF THE DRAWINGS

FIGS. 2A-2I schematically illustrate one embodiment of a triggered RNAi system. There are three synthetic nucleic acid hairpin strands, A, B, and C shown. Hairpins A, B and C of FIGS. 2A-2I co-exist metastably and do not induce RNAi action on their own. The mRNA "detection target" is D (comprising sequence regions b*-x*-a*). When D is present in the system, it activates A, which in turn catalyzes B and C to form the RNA duplex B.C.

FIG. 3 schematically illustrates one embodiment of a triggered RNAi system. Duplex B.C from FIG. 2I is recognized and processed by Dicer to silence the mRNA "silencing target" S (comprising sequence regions c-y-z). Note that the mRNA detection target D and the mRNA silencing target S have completely independent sequences.

FIG. 6 illustrates a detection target T that interacts with and opens an initiator monomer (initiator) A. In the absence of the mRNA "detection target" T, hairpin A, complex C.E, and complex B.D co-exist metastably and do not induce RNAi action on their own. The bulge loops on C.E and B.D possess regions (y and y*, respectively) that are complementary to one another. T comprises sequence regions (a)-(w)-(b)-(s). When T is present in the system, it activates A, and the complex T.A is formed. T.A, in turn, reacts with C.E and B.D to form T.A.B.C.D.E. This leads to the formation of the RNA duplexes B.C and D.E. Duplex D.E is recognized and processed by Dicer to silence an mRNA "silencing target" comprising sequence regions (x)-(z).

FIG. 11A illustrates that when the target is present, a triggered RNAi system is activated that leads to the silencing of green fluorescent protein (GFP). FIG. 11B schematically illustrates that when the target is present, a triggered RNAi system is activated that leads to the silencing of a repressor gene that modulates the expression of GFP.

DETAILED DESCRIPTION OF THE PREFERRED EMBODIMENTS

Figure 1:
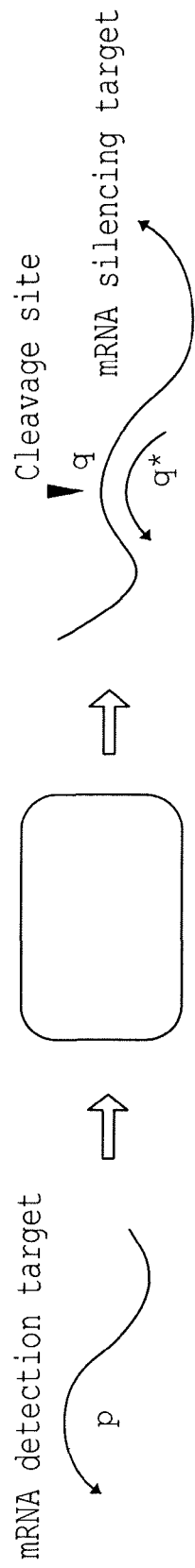
FIG. 1 schematically depicts a summary of logical operation of the triggered RNAi pathway. Each letter (i.e., p and q) represents a region of nucleic acids. Letters marked with an asterisk (*) are complementary to the corresponding unmarked letter.

Various embodiments disclosed herein are generally directed towards methods of detecting the presence of detection targets using triggered RNAi.

Triggered RNAi mechanisms can be used, for example, for the specific detection of targets ("detection targets") by modulating the expression of a marker gene (e.g., green fluorescent protein (GFP)). GFP (Shimomura et al., J. Cell Comp. Physiol. (1962) 59:223-239) together with other fluorescent proteins have revolutionized biology and largely defined modern in vivo fluorescence microscopy (Zimmer, Prometheus Book (2005). Currently, to monitor the expression of a target gene, a GFP tag is structurally coupled to the protein coded by the target gene. For each target protein, a plasmid must be constructed to enable concatenation of the GFP gene with the target gene within the cell. In some cases, the resulting structural linkage between the GFP and the target protein impedes the folding or function of the target.

Using triggered RNAi, the level of target (e.g., mRNA transcript level) can be linked with the expression level of a structurally independent marker gene (e.g., GFP). For example, if the desired target gene is detected, GFP (or other marker gene) expression can be suppressed (or activated) via triggered RNAi.

The triggered RNAi approaches described herein retain the logical link between the target gene and the marker gene (e.g., the GFP gene) but avoid the structural link. The structural decoupling using triggered RNAi methods does not require tedious plasmid construction for each new target. In addition, the structural decoupling using triggered RNAi approaches does not require the presence of a protein tag (e.g., GFP tag) fused to a target gene. For example, a drawback of the use of a GFP fusion protein is that the presence of a GFP structural tag may affect the normal expression and function of the target protein. In addition, the structural decoupling using triggered RNAi processes eliminates the need for the tedious cloning step to make the fusion protein (e.g., a target-GFP fusion protein). Using triggered RNAi approaches described herein, modulation of marker expression can be achieved by introducing the triggered-RNAi molecules (e.g., hairpins) that logically link the detection target gene expression to expression of a marker gene (e.g., GFP), exogenously or endogenously. In some embodiments, the intrinsic signal amplification by triggered RNAi mechanisms can allow for the visualization of low copy genes.

At present, there are a limited number of techniques that exist for RNAi. Various RNAi techniques have been restricted in utility because it has not been possible to use RNAi to silence targets in response to the presence of other, perhaps unrelated molecules. While up to 100-fold enhancements in silencing potency have been achieved by using longer RNA duplexes that are processed into siRNAs by Dicer prior to incorporation into RISC (Kim et al., 2005, Nat. Biotechnol. 23(2): 222-226), the ability for catalytic amplification of RNAi has been limited. Some of the embodiments described herein overcome these and other limitations.

Triggered RNAi has been developed based on the triggered hybridization of nucleic acid molecules, typically starting from monomer hairpins (U.S. Patent Publication No. 2008/0214488 and PCT Publication No. WO 2008/106658, which are hereby incorporated by reference in their entireties). In the triggered RNAi process, a detection event is transduced into the formation of a distinct inactivator dsRNA. Monomers can be used that generate inactivator dsRNAs in the presence of a detection target. The inactivator dsRNAs can be used for gene silencing. For example, in some embodiments, the inactivator dsRNAs can be processed by Dicer into siRNAs. Once formed, the siRNAs can lead to silencing of one or more silencing targets. The silencing of one or more silencing targets can modulate the expression of one or more marker or reporter molecules (e.g., the expression of GFP). For example, expression of the reporter gene itself can be reduced or expression of a gene that in turn modulates expression of the reporter gene can be reduced. Triggered RNAi is much more versatile than traditional RNAi, because the sequence of the silencing target is not limited to the sequence of the detection target. Thus, there does not have to be any relationship between the detection target and a marker whose expression is to be modulated when the target is present. In some embodiments, detection targets other than nucleic acid molecules can trigger RNAi. In some embodiments, the triggered RNAi system can be catalytic, and the detection binding event can be amplified to silence one or more silencing targets.

Triggered RNAi can be used, for example, for the specific detection of targets ("detection targets"). In some embodiments, the detection targets are associated with a disease or disorder. The detection targets, which can be found, for example, exclusively in diseased cells or to a greater extent in diseased cells than in healthy cells, can act as a trigger for RNAi silencing of silencing targets. Silencing targets can be, for example, marker or reporter genes or mRNA encoding a marker or reporter molecule (e.g., GFP). Silencing targets may also be, for example, genes involved in the modulation of expression of the marker gene. Genes that modulate expression of a reporter gene may increase or decrease reporter gene expression. Thus, silencing of the modulatory gene may increase or decrease reporter gene expression. Examples of such genes include, but are not limited to, transcription factors, repressors, activators, and enhancers. These genes may be endogenous genes or exogenous. In some embodiments the marker gene and the regulatory gene may be transfected together into cells in which the presence of a particular target is to be evaluated.

In some embodiments, a disease or disorder can be diagnosed by targeting diseased cells and silencing selected genes. The triggered RNAi methods described herein are not limited to diagnosing diseases or disorders. The methods described herein can be used in any context where it is desirable to modulate expression of a marker or reporter gene when a molecule of interest is present in a system. For example, the methods can be used in reconstituted in vitro systems. The gene or mRNA can be, for example, endogenous or exogenous mRNA.

Methods and compositions for triggered RNAi are provided. The methods can be conducted, for example, in vitro, in situ, ex vivo, and in vivo. The methods can also be used in on-chip and microarray assays and applications. A schematic depiction of the logical operation of one embodiment of a triggered RNAi process is shown in FIG. 1. In FIG. 1, an mRNA detection target p is present in a sample or cell. Detection of the detection target p by the triggered RNAi pathway results in silencing of mRNA silencing target q (e.g., GFP or a gene that modulates the expression of GFP (e.g., a repressor)). In various embodiments, methods of silencing a target gene are provided. In some embodiments, the methods comprise providing an initiator, a first monomer, and a second monomer to a sample comprising a detection target p, a silencing target gene q, and a marker gene (e.g., GFP). In some embodiments, the marker gene is identical to the silencing target gene. In some embodiments, the marker gene is different from the silencing target gene. Preferably, the detection target p is different from the silencing target gene q. The initiator can bind to a portion of the detection target p. In preferred embodiments, binding of the detection target p can induce a conformational change in the initiator and expose a region of the initiator that can recognize and bind the first monomer. In some embodiments, binding of the initiator to the first monomer can induce a conformational change in the first monomer and expose a region of the first monomer that can recognize and bind the second monomer. In some embodiments, binding of the first monomer to the second monomer can produce an inactivator dsRNA which can silence the silencing target gene q. Preferably, the sequence of the mRNA silencing target q is independent of the detection target p.

One embodiment of a method for triggered RNAi is generally outlined in FIGS. 2 and 3. In FIGS. 2A-2C, a detection target (denoted "D") has a region a* which pairs with region a of hairpin A and induces a strand displacement interaction resulting in the formation of complex D.A. The complex D.A. has a newly exposed single-stranded tail that contains the sequence y*-c*-b*, hereinafter referred to as the initiator region "I". As shown in FIGS. 2D-F, the initiator region I of the D.A complex nucleates at the sticky end b of hairpin B, and induces a strand displacement interaction to open B and expose the single-stranded tail z*-y*-c* (for visual simplicity, only the I portion of the complex D.A is depicted). As shown in FIG. 2H, the I.B complex nucleates at the sticky end c of hairpin C (FIG. 2G) and opens C. As shown in FIG. 2I, hairpin C subsequently displaces I to form complex B.C. As shown in FIG. 3A, complex B.C contains a duplex substrate that can be processed by Dicer. The duplex substrate portion of B.C is recognized by Dicer and processed to induce RNAi action (FIGS. 3A-B). This results in the silencing of a silencing target gene (denoted "S") comprising the sequence c-y-z. The silencing target gene S is independent of the mRNA detection target D. I is available to start another cycle amplifying reaction. Other embodiments of methods for triggered RNAi are outlined in FIGS. 4-10. In some embodiments, non-hairpin monomers can be used (see, e.g., FIG. 7). In other embodiments, nucleic acid complexes can be used. In some embodiments, dicer substrates are formed. In other embodiments, RISC substrates (e.g., siRNA) are formed. Some embodiments describe catalytic methods. One example of a catalysis is when multiple dicer substrates can be created with one target (see, e.g., FIG. 4).

In some embodiments, methods are provided for triggered RNAi silencing of multiple genes. Such triggered RNAi methods would implement the logical operation: if detection target p is detected, silence genes $q_1$, $q_2$, $q_3$ . . . For example, in some embodiments, an inactivator dsRNA can be processed to silence multiple gene targets. These methods can be used, for example, to create silencing networks in which multiple genes are being detected, each leading to the silencing of some number of other genes. One or more of the mRNA detection targets and mRNA silencing targets could coincide. In additional embodiments, multiple marker genes can be modulated by the silencing of multiple genes to achieve multiplexed RNAi imaging or multiplexed reporter systems. In some embodiments, the expression of two or more marker genes is modulated when a target is present. The expression of both marker genes may be increased or decreased, or the expression of one may be increased and the other decreased. In further embodiments, molecular logic can be embedded in the triggering mechanism such that the profile of a combination of genes can be identified and results in a specific signal change of the marker or reporter.

In other embodiments, methods are provided for triggered RNAi involving detection of a non-mRNA target. For example, triggered RNAi could be activated by using a conformation-switching aptamer that exposes an initiator region upon binding to a target protein or small molecule. The initiator region would then catalyze the formation of the dsRNA substrates as with the triggered RNAi mechanism shown in FIGS. 2 and 3. The experimental selection of conformation switching aptamers has been previously demonstrated (See, for example, Jhaveri et al., 2000*, Nat. Biotechnol.* 18: 1293-1297.

In some embodiments, triggered RNAi can be combined with an nucleic acid exponential amplifier scheme, such as the scheme disclosed in U.S. Publication No. 2005-0260635, filed Mar. 22, 2005, to achieve even higher amplification.

In some embodiments, methods are provided for triggered RNAi silencing of an exogenous gene (e.g., an mRNA). In some embodiments, methods are provided for triggered RNAi silencing of an endogenous gene (e.g., an mRNA). Endogenous gene can include genes native to a cell's genome and genes that have been integrated into a cell's genome (e.g., a host cell's genome). In some embodiments, methods are provided for triggered RNAi silencing of an mRNA encoding a marker or reporter molecule, such as, for example, green fluorescence protein (GFP) and other imaging or diagnostic markers. In some embodiments, methods are provided for triggered RNAi silencing of an mRNA encoding any protein that can readily be measured or that can readily generate a detectable signal. The detection of a detection target of interest can thus result in a change of the reporter signal via triggered RNAi. The reporter signal or change in signal can be a measured in a variety of ways known in the art. For example, a reporter signal can be measured directly (e.g., a visual GFP signal) or indirectly (e.g., by western blot to determine protein levels).

The above and additional embodiments are discussed in more detail below, after a brief discussion of some of the terms used in the specification

DEFINITIONS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Unless otherwise defined, scientific and technical terms used in connection with the invention described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques of described herein are those well known and commonly used in the art.

As utilized in accordance with the embodiments provided herein, the following terms, unless otherwise indicated, shall be understood to have the following meanings:

The term "nucleic acid" refers to natural nucleic acids, artificial nucleic acids, analogs thereof, or combinations thereof. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

As used herein, the terms "polynucleotide," "oligonucleotide," and "nucleic acid oligomers" are used interchangeably and mean single-stranded and double-stranded polymers of nucleic acids, including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of nucleobase and sugar analogs. Polynucleotides typically range in size from a few monomeric units, e.g. 5-40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

A "gene" (e.g., a marker gene) or "coding sequence" or a sequence, which "encodes" a particular protein, is a nucleic acid molecule which is transcribed (in the case of DNA) and translated (in the case of mRNA) into a polypeptide in vitro or in vivo when placed under the control of appropriate regulatory or control sequences. The boundaries of the gene are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and even synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, repressors, and the like, which collectively provide for the replication, transcription and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

The term "operably linked" refers to an arrangement of elements, wherein the components so described are configured so as to perform, their usual function. Thus, control elements operably linked to a coding sequence (e.g., the coding sequence of a marker gene) are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

As used herein "double stranded RNA," and "dsRNA" are used interchangeably and refer to a polynucleotide having two complementary strands of RNA.

An "inactivator dsRNA" is a dsRNA that can silence a silencing target. In some embodiments, an inactivator dsRNA can be processed by Dicer to form siRNAs. In some embodiments, an inactivator dsRNA can comprise an siRNA. In some embodiments, an inactivator dsRNA can silence a silencing target by activating PKR.

An "RNA duplex substrate" is an inactivator dsRNA that can processed by Dicer and/or RISC.

The term "hairpin" and refers to a structured formed by intramolecular base pairing in a single-stranded polynucleotide ending in an unpaired loop. A "hairpin loop" refers to a single stranded region that loops back on itself and is closed by a single base pair.

"Interior loop," "internal loop," and "bulge loop" are used interchangeably and refer to a loop in which the single-stranded portion of a loop is bordered by two base pairs, one on each side.

The term "sticky end" refers to a nucleic acid sequence that is available to hybridize with a complementary nucleic acid sequence. A "sticky end" is located at an end of a double-stranded nucleic acid. The secondary structure of the "sticky end" is preferably such that the sticky end is available to hybridize with a complementary nucleic acid under the appropriate reaction conditions without undergoing a conformational change. In some embodiments the sticky end is preferably a single stranded nucleic acid.

"Monomers" as used herein refers to individual nucleic acid oligomers. Typically, each monomer comprises at least one region that is complementary to at least one portion of another monomer being used for the triggered RNAi process. The makeup of the monomers for some embodiments is described in more detail below. Two or more monomers can associate (e.g. by hybridization) to form a complex. For example, a complex can comprise two nucleic acid monomers that share a region of complementarity. In embodiments described herein using one or more monomers, complexes can be substituted for monomers such that the embodiments can use monomers or complexes or combinations of monomers and complexes. Complexes can comprise two or more nucleic acid strands. Complexes can comprise two complementary or substantially complementary strands. Complexes can comprise various secondary structures. For example, complexes can comprise a bulge loop structure that is closed by two nucleic acid base pairs.

"Triggered RNAi monomers" are monomers that are able to assemble to form an inactivator dsRNA upon exposure to an activated initiator.

"Substrate monomers" are monomers that can form a duplex comprising an inactivator dsRNA. Typically two substrate monomers form an RNA duplex having a dsRNA region which can be used by RNAi machinery to silence a silencing target.

An "initiator region" is a region on a molecule that is able to initiate the formation of RNA duplexes from monomers. Preferred initiator regions comprise a sequence that is complementary to the initiator complement region of a substrate monomer.

An "initiator" is a molecule that is able to interact with a detection target and subsequently expose an initiator region. Preferred initiators comprise a detection target binding region that is complementary to or otherwise recognize a portion of a detection target, and an initiator region. Before the initiator interacts with a detection target, the initiator region is not exposed and therefore not available to hybridize to an initiator complement region. In some embodiments the detection target binding region can comprise a sticky end. Other embodiments of the initiator comprise a recognition molecule that binds or interacts with a detection target. In some embodiments the initiator can comprise an aptamer that recognizes a specific molecule, and the aptamer can comprise the detection target binding region.

Interaction of the detection target to the detection target binding region or to the recognition molecule of the initiator begins the triggered RNA process by exposing the initiator region. An "activated initiator" is an initiator that is bound to a detection target. In some embodiments, the initiator can comprise a monomer. In some embodiments, the initiator can be a monomer linked to a recognition molecule.

The initiator region of the initiator is preferably only available to hybridize with the initiator complement region of a substrate monomer when an initiator has been activated by an interaction between the initiator and the detection target. In some embodiments, the initiator hybridizes with the initiator complement region of a second monomer which in turn interacts with a substrate monomer. The substrate monomer preferably comprises a silencing target complement region that is able to hybridize to a silencing target region of another substrate monomer. Preferably, the silencing target complement region of a substrate monomer is different from the detection target binding region of an initiator. In some embodiments, the silencing target complement region of a substrate monomer can be the same as or overlap with the initiator complement region.

In addition, the silencing target complement region of a first substrate monomer is preferably only available to hybridize with the silencing target region of another substrate monomer when the first substrate monomer has already hybridized to an initiator, or an intervening monomer that is made available by the initiator, as discussed in more detail below.

A "detection target" is a molecule of interest, or a combination of molecules of interest, whose presence can activate an initiator that can initiate RNAi and thus modulate marker expression. In some embodiments, the expression of the marker can be modulated and measured directly. In other embodiments, the expression of a marker can be measured indirectly based on a change in measurable activity associated with modulating the marker. Preferred detection targets can be associated with a disease or disorder. In some embodiments, the detection target can be a molecule, or combination of molecules, that is recognized by the initiator, such that the initiator region of the initiator is made available to interact with another monomer. The detection target can be a nucleic acid or any other type of molecule.

An "initiator binding site" is a site on a detection target that can bind to an initiator. Preferably, the initiator binding site is complementary to the detection target complement site of an initiator.

A "silencing target" is a gene of interest, or a combination of genes of interest, that can be silenced by triggered RNAi. Silencing refers to the modulation of the expression of a nucleic acid (e.g., a gene or mRNA). Silencing can refer, for example, to a decreased expression, a reduction of expression, a prevention of expression, or an inhibition of expression of a nucleic acid (e.g., an mRNA silencing target). Preferably, silencing targets can be mRNA. The mRNA can be endogenous or exogenous mRNA. In some embodiments, the silencing target gene can encode a protein that modulates the expression of a marker or reporter gene. In some embodiments, the silencing target can comprise a marker or reporter gene. A "marker gene" refers to any gene or portion of a gene whose level, level of expression, or change in level of expression can be detected.

"Metastable monomers" refer to monomers that, in the absence of a detection target, are kinetically disfavored from associating with other monomers comprising complement regions. In the absence of a detection target, stable monomers are at equilibrium and do not with other monomers comprising complement regions.

As used herein, "polymerization" refers to the association of two or more monomers to form a polymer. The "polymer" may comprise covalent bonds, non-covalent bonds or both. For example, in some embodiments two species of monomers are able to hybridize to form a polymer comprising an RNA duplex substrate.

A "target cell" is a cell that contains or may contain a detection target for triggered RNAi. Examples of target cells include, for example without limitation, cells that contain a nucleic acid signature for a disease, such as, for example, mutant mRNA or fusion mRNA entities. Other examples include, but are not limited to, cells that contain higher-than-background levels of mRNA, peptides, polypeptides, antibodies or fragments thereof, signal cascade molecules, viral particles, bacteria and parasitic organisms.

Exemplary Embodiments

As noted above, RNAi has been adopted as an important tool to study and manipulate gene expression. However, until now, silencing of genes has been limited by the sequence of the inactivator dsRNA. For example, silencing targets are limited to the sequences present in the inactivator dsRNA introduced to the cell or sample.

In some embodiments, methods are provided for triggered RNAi silencing of one or more genes based on the detection of at least one detection target, leading to modulation of marker gene expression. If a gene of interest is present, marker gene expression is modulated. Thus, in some embodiments, the triggered RNAi approach implements the logical operation: if detection target p is detected, silence gene q, which modulates the expression of one or more markers. In other embodiments, methods are provided for triggered RNAi silencing of multiple genes. Such triggered RNAi processes would implement the logical operation: if detection target p is detected, silence genes $q_1, q_2, q_3 \ldots$ The silencing of one or more silencing target genes can modulate the expression of one or more marker genes. Multiple markers can be modulated in a variety of ways.

In some embodiments, the expression of one or more markers can be increased. In other embodiments, the expression of one or more markers can be decreased. In further embodiments, the expression of one or more markers can be increased and the expression of one or more markers can be decreased simultaneously.

Figure 11A:
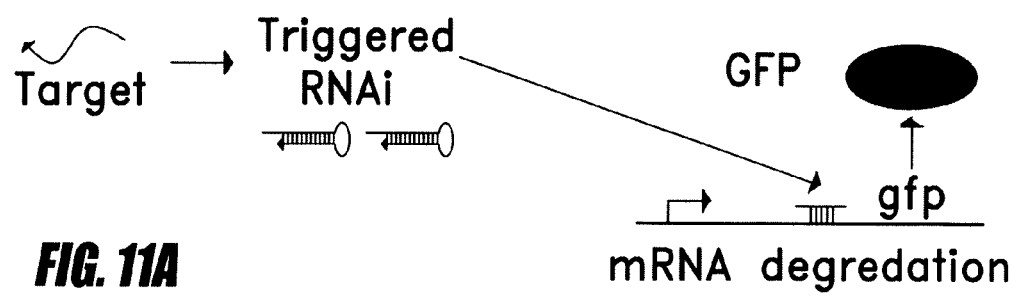
FIGS. 11A and 11B schematically illustrate applications of triggered RNAi systems.

In some embodiments, the silencing target gene can comprise the marker gene, and the detection of the detection target results in suppression (e.g., silencing, degradation, and/or reduced expression) of the marker gene. This is described, for example, in FIG. 11A. FIG. 11A illustrates a negative detection scheme, in which the presence of target mRNA suppresses GFP expression by degrading the GFP mRNA.

Figure 11B:
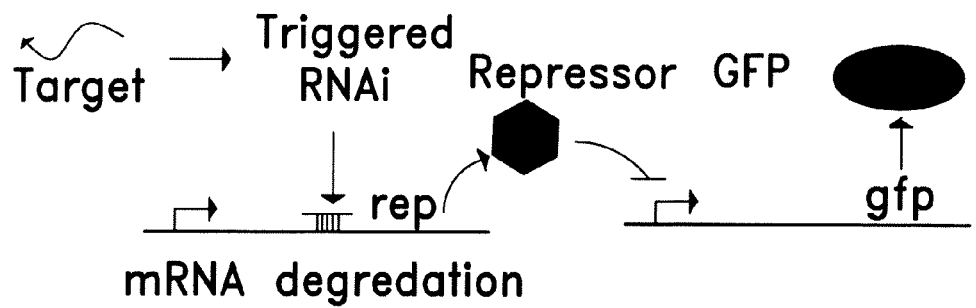

In other embodiments, the expression of the marker gene is modulated by the silencing of a silencing target gene that is different from the marker gene (e.g., a control element for the marker gene such as a repressor). For example, FIG. 11B illustrates a positive detection scheme, in which the presence of target mRNA down regulates expression of a repressor protein that binds to a GFP gene, and hence increases GFP expression. In other embodiments, the expression of a marker gene can be suppressed by the silencing of a silencing target gene that is different from the marker gene (e.g., an enhancer of the marker gene).

In some embodiments of triggered RNAi, three or more metastable monomer hairpins are used. The hairpins may comprise loops that are protected by long stems. Hairpin monomers can comprise hairpin loops that are closed by a single base pair. In some embodiments, the loops can be resistant to invasion by complementary single-stranded nucleic acids. This stability allows for the storage of potential energy in the loops. Potential energy is released when a triggered conformational change allows the single-stranded bases in the loops to hybridize with a complementary strand, preferably in a second hairpin monomer. Each monomer is caught in a kinetic trap, preventing the system from rapidly equilibrating. See, for example, Dirks, R. and N. Pierce, *Proc. Natl. Acad. Sci. USA* 101(43): 15275-15278 (2004), and U.S. patent application Ser. No. 11/087,937, filed Mar. 22, 2005 (published as U.S. Publication No. 2005-0260635 on Nov. 24, 2005), each of which is incorporated herein by reference in its entirety. Thus, pairs of substrate monomers are unable to form an inactivator dsRNA in the absence of a detection target. In some embodiments, the inactivator dsRNA is a Dicer substrate. In other embodiments, the inactivator dsRNA is a RISC substrate (e.g., siRNA itself).

In some embodiments, introduction of one or more detection targets causes the monomers to undergo a series of hybridization events to form an RNA duplex substrate that can be processed by Dicer and subsequently lead to silencing of one or more silencing targets. In other embodiments, a RISC substrate (e.g., siRNA itself) is formed. In some embodiments, triggered RNA monomers can polymerize in the presence of detection targets such as cancer related mRNA sequences or viral nucleic acids and form an RNA duplex substrate. Triggered RNAi leads to gene silencing of one or more silencing targets in cells comprising the detection target, for example diseased cells comprising a disease-associated detection target. The silencing of one or more silence targets will modulate the expression of one or more marker genes, thereby allowing detection of one or more detection targets.

In some embodiments the methods comprise administering to target cells in the patient, such as tumor cells, an effective amount of triggered RNAi monomers, one of the monomers being an initiator having a detection target binding region. For example, the detection target binding region of an initiator may be at least 90% complementary to a detection target region of a nucleic acid that is associated with the disease, such as an mRNA associated with the cancer or a viral-associated nucleic acid. In some embodiments, the detection target binding region can be completely complementary to a detection target region of a nucleic acid that is associated with the disease. In some embodiments, the initiator is an aptamer that recognizes a disease-associated molecule. In some embodiments an aptamer is identified that is able to specifically bind a detection target. The detection target is not limited to a nucleic acid but may be, for example, a polypeptide or small molecule. In some embodiments the aptamer is linked to an initiator region in such a way that the initiator region is unavailable to stimulate formation of inactivator dsRNAs in the absence of detection target binding to the aptamer. Preferably, conformation changes in the aptamer secondary structure expose the initiator region. In some embodiments, such an aptamer initiator is a hairpin nucleic acid that comprises an initiator region that is complementary to the sticky end of a substrate monomer and a region of the substrate monomer adjacent to the sticky end, a loop region and an aptamer sequence. The hairpin aptamer initiator may also comprise a region that enhances the stability of the hairpin in the absence of aptamer binding to the detection target.

Detection targets can be any molecule of interest to be used in conjunction with triggered RNAi. In some embodiment a detection target can be an oncogenic mRNA such as an mRNA associated with, for example, a glioma or Ewing's sarcoma. Such mRNAs are disclosed in, for example, Shir, A., and A. Levitzski, *Nature Biotechnology* 20:895-900 (2002); Dohjima, T. et al., *Molecular Therapy* 7: 811-816 (2003), each of which is herein incorporated by reference in its entirety. In other embodiments, the detection target can be a fusion sequence associated with tumors. Examples of fusion sequences are provided in, for example, Kim et al., *Nucleic Acids Research* 34: D22-D24 (2006), which is herein incorporated by reference in its entirety. In some embodiments, the detection target can be endogenous mRNA or naturally occurring mRNA. In other embodiments, the detection target can be exogenous mRNA or mRNA provided to the cells. For example, the methods described herein can be used to identify cells expressing a transgene, such as cells that were successfully transfected using, for example, gene therapy techniques. Such methods can be used to determine, for example, transfection efficiencies and whether the intended cells were successfully transfected.

In some embodiments, triggered RNAi monomers may be designed to form an inactivator dsRNA in the presence of, for example, a viral gene transcript. In some embodiments, a patient to be diagnosed can be infected with, for example, the human immunodeficiency virus.

Monomers

Two or more distinct species of nucleic acid monomers can be utilized in a triggered RNAi process. In some embodiments, preferably three or more distinct species of nucleic acid monomers are utilized in a triggered RNAi process. In the methods described herein, the monomers can be, for example, RNA, DNA or RNA-DNA hybrid monomers. Each monomer species typically comprises at least one region that is complementary to a portion of another monomer species. However, the monomers are designed such that they are kinetically trapped and the system is preferably unable to equilibrate in the absence of an activated initiator that can disrupt the secondary structure of one of the monomers. Thus, the monomers are preferably unable to form an inactivator dsRNA in the absence of an activated initiator. Hybridization of an initiator region of an activated initiator to a substrate monomer, or to an intervening monomer that in turn reacts with a substrate monomer, initiates a reaction of kinetic escapes by the monomer species resulting in formation of an inactivator dsRNA. In the examples below, substrate monomers and/or complexes interact in the presence of an activated initiator to form an inactivator dsRNA.

In some embodiments, the initiator can be a monomer. An initiator is preferably unable to trigger formation of an inactivator dsRNA from the other monomers in the absence of a detection target. In some embodiments, the initiator can comprise a hairpin monomer. In some embodiments, the initiator can comprise an aptamer. In some embodiment, the aptamer can comprise the detection target binding region. In some embodiments, the initiator can comprise a recognition molecule. In some embodiments, the initiator can be a conformation-switching aptamer that exposes an initiator region upon binding to a target protein or small molecule.

In some embodiments, the initiator can comprise a substrate monomer.

In some embodiments, one or more monomer species are employed that have a hairpin structure. In some embodiments, three monomer species are employed that have a hairpin structure. In other embodiments, one monomer species is employed that has a hairpin structure.

In some embodiments, the hairpin monomers can comprise loops protected by long stems. In other embodiments, monomers with a different secondary structure are provided. However, in some embodiments, the secondary structure is preferably such that the initiator monomers are metastable or stable in the absence of a detection target and the substrate monomers do not react under the reaction conditions in the absence of an activated initiator that is able to initiate formation of inactivator dsRNA. In some embodiments, at least three monomer species or complexes or combinations thereof including an initiator, a first substrate monomer and a second substrate monomer are used. In some embodiments, in the presence of a detection target, the secondary structure of an initiator can change such that it is able to hybridize to a first substrate monomer species. This in turn preferably leads to a change in the secondary structure of the first substrate monomer, which is then able to hybridize to a second substrate monomer species and form an RNA duplex comprising an inactivator dsRNA region. In some embodiments, the inactivator dsRNA can be an RNA duplex substrate for RNAi, such as a substrate for Dicer. In other embodiments, inactivator dsRNA is siRNA (RISC substrate). In some embodiments, the second substrate monomer is able to displace the first substrate monomer from the initiator once the first substrate monomer has hybridized to the second substrate monomer. In this way, the activated initiator can be recycled and used to initiate formation of more RNA duplex substrates for Dicer. Thus, in the presence of one or more detection targets, multiple RNA duplex substrates can be produced.

A number of criteria can be used to design the monomers to achieve the desired properties. These include, for example and without limitation, sequence symmetry minimization, the probability of adopting the detection target secondary structure at equilibrium, the average number of incorrect nucleotides at equilibrium relative to the target structure, hybridization kinetics, and the silencing target sequence. The composition of the monomers is not limited to any particular sequences or number of bases, and is designed based on the particular detection and silencing targets of the particular triggered RNAi reaction.

Monomers can be synthesized using standard methods, including commercially available nucleic acid synthesizers or obtained from commercial sources such as Integrated DNA Technologies (Coralville, Iowa).

In some embodiments, the monomers are RNA monomers. In some embodiments, the monomers can be RNA-DNA hybrids. In some embodiments, the monomers comprise a protein-binding region, or other recognition molecule. In some embodiments, the monomers can contain a fluorophore, luminescent molecule, calorimetric compound or other component that allows the resulting polymers to be visualized. In embodiments using one or more monomers, complexes can be substituted for monomers such that the embodiments can use monomers or complexes or combinations of monomers and complexes.

In some embodiments, at least three RNA hairpin monomers are utilized as illustrated in FIGS. 2 and 3. In the depicted embodiment, the monomers are denoted "A" (FIG. 2B), "B" (FIG. 2E) and "C" (FIG. 2G). The monomers each preferably comprise a sticky end, a hairpin loop region at the opposite end of the sticky end, and two "stems regions," a first stem region and a second stem region, that together can form a duplex region. The small letters represent sequence segments. Letters marked with an asterisk (*) are complementary to the corresponding unmarked letter.

In preferred embodiments, the first stem region of a monomer can hybridize to the second stem region of the monomer to form the hairpin structure. For example, as shown in FIG. 2B, the monomer (A) comprises a first stem region comprising a region (x-b) that is able to hybridize to the second stem region (b*-x*). In some embodiments, in the absence of a detection target, the first and second stem regions of each monomer are generally hybridized to form a duplex region of the monomer.

In the depicted embodiment, a monomer (A) (hereinafter referred to as the "initiator") comprises a "detection target binding region" (comprising the sequence a-x-b) and an "initiator region" comprising the sequence y*-c*-b*. In the depicted embodiment, a first substrate monomer (B) comprises an "initiator complement region" b-c-y and a "silencing target complement region" (comprising the sequence z*-y*-c*). In the depicted embodiment, a second substrate monomer C comprises a "silencing target region" (comprising the sequence c-y-z) and a "recycling region" having the same sequence as the initiator region of the initiator (comprising the sequence y*-c*-b*).

Figure 2A:
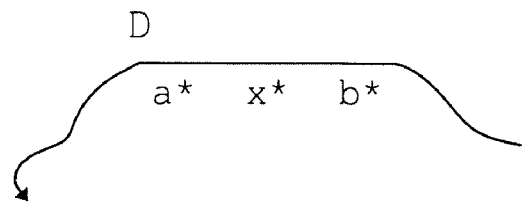
Figure 2B:
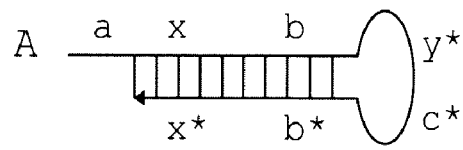
Figure 2C:
Figure 2C:
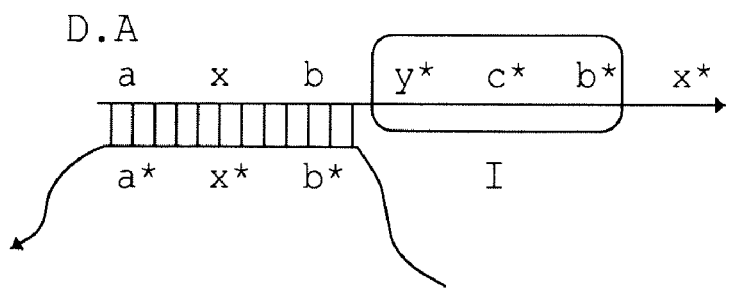

The detection stage of some embodiments of triggered RNAi is depicted in FIGS. 2A-2C. A region (b*-x*-a*) of the detection target (D) and the detection target binding region (a-x-b) of the initiator (A) are typically substantially complementary. That is, the region (b*-x*-a*) of the detection target (D) is able to hybridize to the detection target binding region (a-x-b) of the initiator (A).

The initiator (A) preferably comprises a sticky end a, which is a portion of the detection target binding region (a-x-b). Sticky end a of the initiator is complementary to a sequence segment a* of a detection target (D; FIG. 2A). In some embodiments, the detector complement region of an initiator can comprise a sticky end and a portion of the first stem region of the initiator. For example, in the depicted figure, the initiator (A) has a detection target binding region a-x-b, where a is a sticky end, and x-b is portion of the first stem region of the initiator.

Preferably, upon hybridization of the detection target to the sticky end of the detector complement region of the initiator, one arm of the hairpin structure is displaced. This opens the hairpin. In the depicted embodiment, the detection target (D)

nucleates at the sticky end a of the initiator (A) by pairing segment a* with a. This induces a strand displacement interaction resulting in the hybridization of the detection target (D) at a region b*-x*-a* to the detection target binding region a-x-b of the initiator (A) to form the first complex (D.A) (FIG. 2C). The detection target may be, for example, any molecule in whose presence, marker or reporter gene expression is modulated, such as a cellular component (such as, for example, a nucleic acid sequence) that is found only in target diseased cells or to a lesser extent in healthy cells, as discussed in more detail below. Detection targets include, without limitation, polypeptides, such as antibodies and antibody fragments, nucleic acids, aptamers, and small molecules. The use of an initiator bound to a recognition molecule is described in more detail below.

In the depicted embodiment, the first complex (D.A) has a newly exposed single-stranded tail that comprises the initiator region (I) having sequence y*-c*-b* of the initiator (A) (FIG. 2C).

In some embodiments, the initiator region of an initiator can comprise a portion of the loop region and a portion of the second stem region of the initiator. For example, in the depicted embodiment, the initiator region (I) of the initiator (A) has a sequence y*-c*-b*, where y*-c* is a portion of the loop region and b* is a portion of the second stem region of the initiator. In the absence of a detection target, the first and second stem regions of the initiator are generally hybridized to form a duplex region of the initiator, and the initiator region of the initiator is generally not available for hybridization to another monomer.

The inactivator dsRNA formation stage of some embodiments of triggered RNAi is depicted in FIGS. 2D-2I. In the depicted embodiment, the first substrate monomer (B) (FIG. 2E) preferably comprises a sticky end b that is complementary to a sequence segment b* of the initiator region (I) of the first complex (D.A) that becomes accessible upon detection target binding to the initiator and opening of the hairpin (FIG. 2D). (For visual simplicity, only the I portion of complex D.A is depicted in FIGS. 2D, 2F, 2H and 2I. However, I remains a portion of complex D.A.) The first substrate monomer (B) has an initiator complement region which is substantially complementary to the initiator region of the initiator. In some embodiments, the initiator complement region of the first substrate monomer comprises a sticky end and a portion of the first stem region of the first monomer. For example, in the depicted embodiment, the first substrate monomer (B) has an initiator complement region b-c-y, where b is a sticky end and c-y is a portion of the first stem region.

Preferably, upon hybridization of the exposed initiator region of the first complex to the sticky end of the initiator complement region of the first substrate monomer, one arm of the hairpin structure is displaced. This opens the hairpin. In the depicted embodiment, the initiator region (I) of the first complex (D.A) nucleates at the sticky end b of the first substrate monomer (B) and induces a strand displacement interaction resulting in the hybridization of the initiator region I (y*-c*-b*) of the first complex (D.A) to the initiator complement region (b-c-y) of the first substrate monomer (B) and formation of a second complex (I.B) (FIG. 2F).

In the depicted embodiment, the second complex (I.B) has a newly exposed single-stranded tail that comprises a silencing target complement region (z*-y*-c*) (FIG. 2F).

In some embodiments, the silencing target complement region preferably can comprise a portion of the loop region and a portion of the second stem region of the first substrate monomer. For example, in the depicted embodiment, the silencing target complement region of the first substrate monomer (B) has a sequence z*-y*-c*, where z* is a portion of the loop region and y*-c* is a portion of the second stem region of the first substrate monomer.

In the absence of an activated initiator, the first and second stem regions of the first substrate monomer are generally hybridized to form a duplex region of the first substrate monomer, and the silencing target complement region is generally not available for hybridization to another monomer. The silencing target complement region of the first substrate monomer is exposed by the opening of the hairpin through binding of the initiator I.

The second substrate monomer (C) (FIG. 2G) preferably comprises a sticky end c that is complementary to a sequence segment c* of the silencing target complement region (z*-y*-c*) of the first substrate monomer (B) that becomes accessible upon the binding of the initiator region (I) of the first complex (D.A) to the first substrate monomer (B) (FIG. 2F). The second substrate monomer has a silencing target region which is substantially complementary to the silencing target complement region of the first substrate monomer. In some embodiments, the silencing target region of a second substrate monomer comprises a sticky end and a portion of the first stem region of the second substrate monomer. For example, in the depicted embodiment, the second monomer (C) has a silencing target region c-y-z, where c is a sticky end and y-z is a portion of the first stem region.

Preferably, upon hybridization of the silencing target complement region of the first substrate monomer to the sticky end of the silencing target region of the second substrate monomer, one arm of the hairpin structure is displaced. This opens the hairpin. In the depicted embodiment, the silencing target complement region of the second complex (I.B) nucleates at the sticky end c of the second substrate monomer (C) and induces a strand displacement interaction resulting in the hybridization of the silencing target complement region (z*-y*-c*) of the second complex (I.B) to the silencing target region (c-y-z) of the second substrate monomer (C) and opening the second substrate monomer (C) (FIG. 2H). In the depicted embodiment, the second substrate monomer (C) has a newly exposed single-stranded tail that comprises the recycling region (y*-c*-b*).

In some embodiments, the second substrate monomer can comprise a recycling region having the same sequence as the initiator region of the initiator. In some embodiments, the recycling region can comprise a portion of the loop region and a portion of the second stem region of the second substrate monomer. For example, in the depicted embodiment, the second substrate monomer has a recycling region y*-c*-b*, where y*-c* is a portion of the loop region and b* is a portion of the second stem region of the second substrate monomer. In the absence of a second complex comprising the initiator and the first substrate monomer, the first and second stem regions of the second substrate monomer are generally hybridized to form a duplex region of the second substrate monomer, and the recycling region is generally not available for hybridization to another monomer. The recycling region of the second substrate monomer is exposed by the opening of the hairpin. The exposed recycling region can bind the initiator complement region of the first substrate monomer, thereby displacing the first complex comprising the initiator such that the initiator can be recycled to react with another first substrate monomer.

In the depicted embodiment, after the hairpin is opened to expose the recycling region of the second substrate monomer, the second substrate monomer (C) subsequently displaces the initiator region (I) of the second complex (I.B) to form a third complex (B.C) (FIG. 2I). The third complex (B.C) comprises an inactivator dsRNA. In the depicted embodiment, the inactivator dsRNA is an RNA duplex substrate that can be processed by the RNAi mechanism in the cell. For example, the inactivator dsRNA can be of a size that can be processed by Dicer. In the depicted embodiment, the RNA duplex substrate is a 27-bp RNA duplex substrate comprising the sequence z*-y*-c*. However, the length of the RNA duplex substrate can vary, and will depend on the design of the substrate monomers used to form the duplex substrate. The composition of the inactivator RNAs is discussed in more detail below.

The sequence of the inactivator dsRNA will depend on the sequence of the portion of the triggered RNA monomers used to form the RNA duplex substrate. The sequence of the triggered RNA monomers can be designed to provide an inactivator dsRNA having a desired sequence. Preferably, the sequence of the inactivator dsRNA comprises at least a portion of the sequence of the silencing target. In some embodiments the entire sequence of the inactivator dsRNA corresponds to a portion of the silencing target sequence.

In some embodiments, after displacement by the recycling region of the second substrate monomer, the displaced initiator region (I) can be used in further inactivator dsRNA formation reactions.

The silencing stage of some embodiments of triggered RNAi is depicted in FIGS. 3A-3B. In the depicted embodiment, the RNA duplex substrate (27-bp RNA duplex substrate) of the third complex (B.C) is recognized by Dicer and processed to induce RNAi action (FIG. 3A). This results in the suppression of the mRNA silencing comprising the target sequence (c-y-z) (FIG. 3B).

Figure 4:
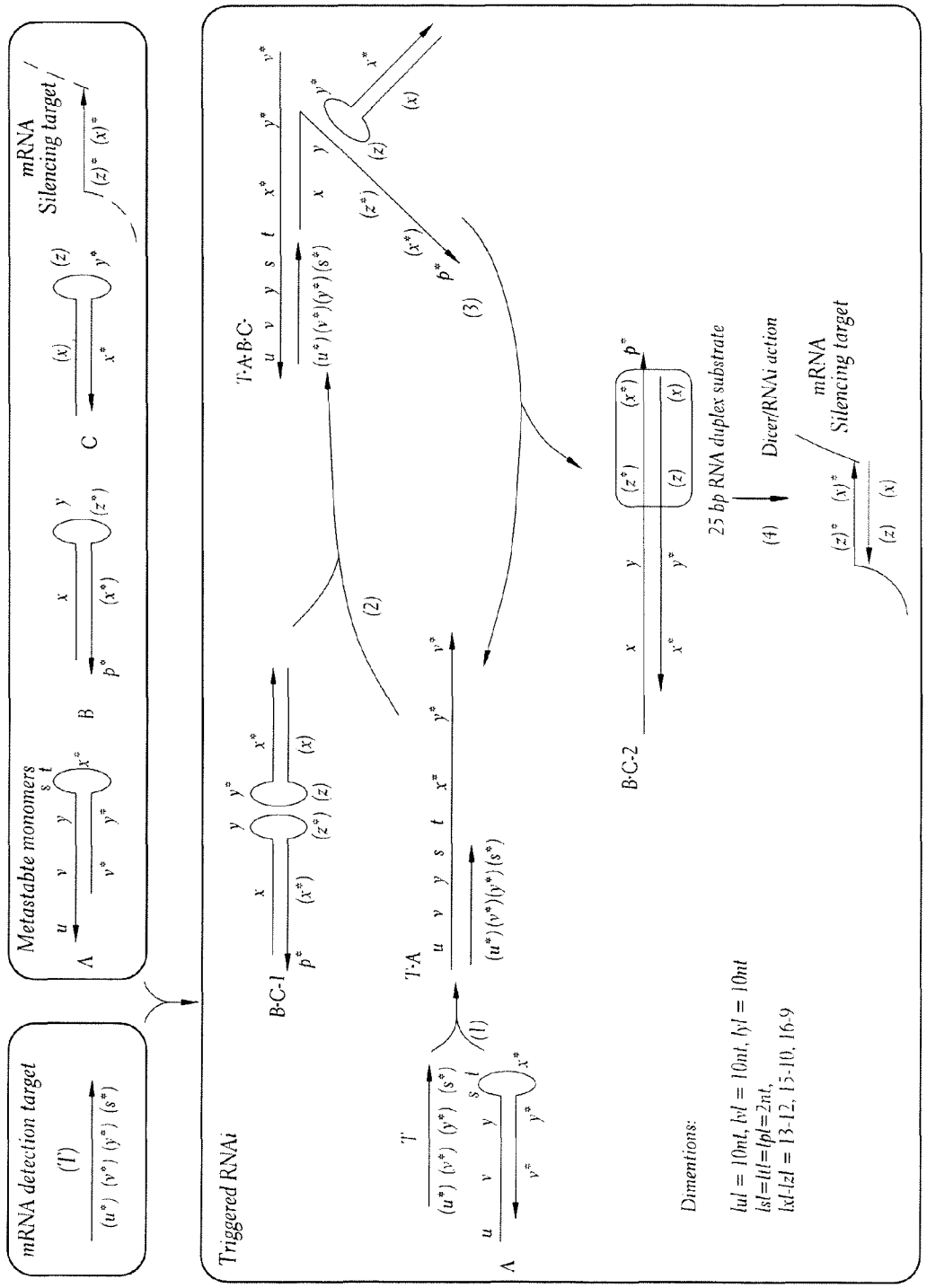
FIG. 4 schematically illustrates another embodiment of a triggered RNAi system using the three synthetic nucleic acid hairpin strands, A, B, and C shown. In the absence of the mRNA "detection target" T, hairpins A, B and C of FIG. 4 co-exist metastably and do not induce RNAi action on their own. The hairpin loops on B and C possess regions that are complementary to one another that allow the formation of B.C-1. T comprises sequence regions u*-v*-y*-s*. When T is present in the system, it activates A, and the complex T.A is formed. T.A, in turn, reacts with B.C-1 to form T.A.B.C. This leads to the formation of the RNA duplex B.C-2. Duplex B.C-2 is recognized and processed by Dicer to silence an mRNA "silencing target" comprising sequence regions (z)*-(x)*.
Figure 5:
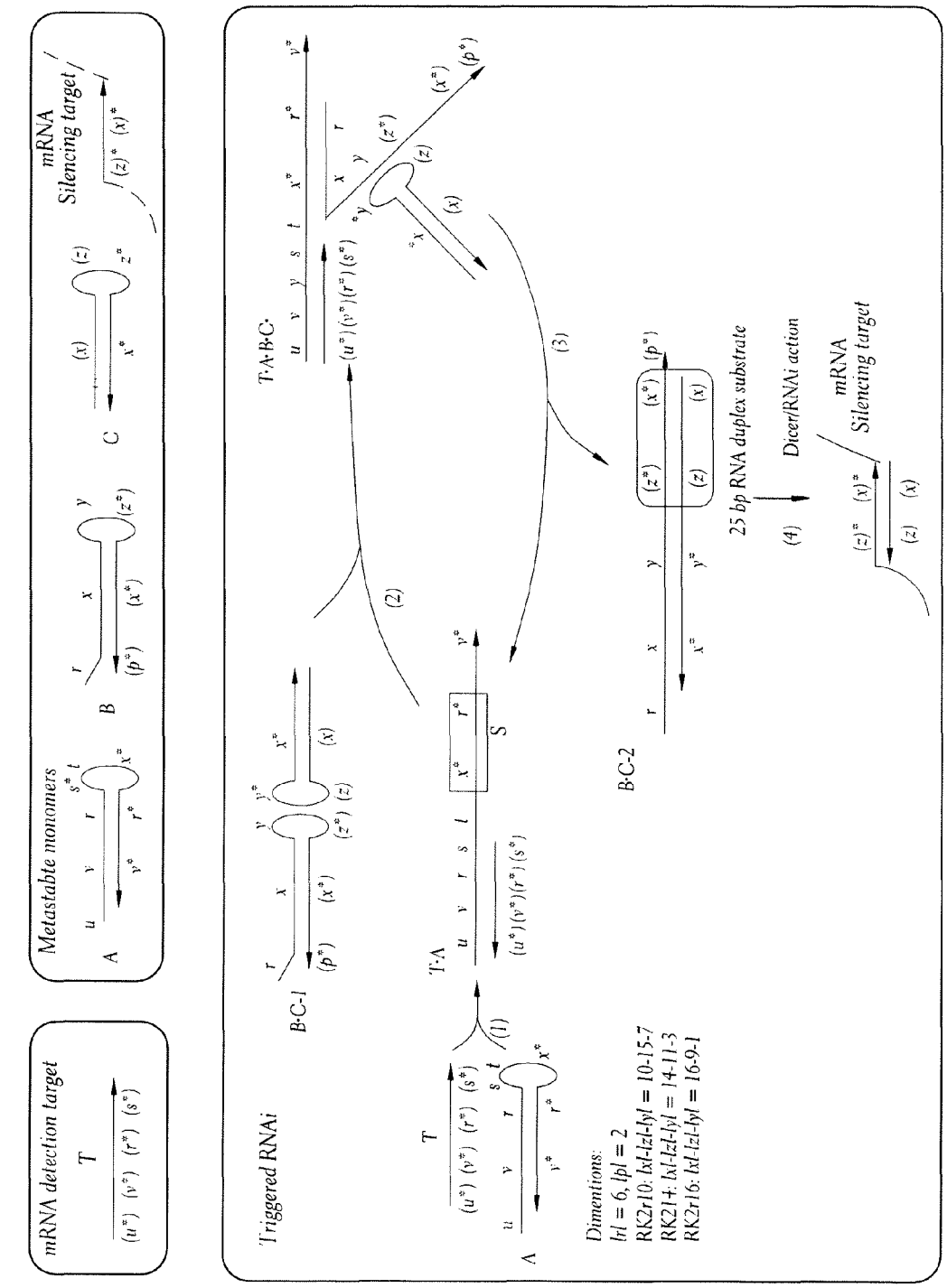
FIG. 5 schematically illustrates another embodiment of a triggered RNAi system using the three synthetic nucleic acid hairpin strands, A, B, and C, shown. In the absence of the mRNA "detection target" T, hairpins A, B and C of FIG. 5 co-exist metastably and do not induce RNAi action on their own. The hairpin loops on B and C possess regions that are complementary to one another that allow the formation of B.C-1. T comprises sequence regions u*-v*-y*-s*. When T is present in the system, it activates A, and the complex T.A is formed. T.A, in turn, interacts with B.C-1 to form T.A.B.C. The presence of a toehold region, r, on B further facilitates the interaction between T.A and B.C-1 to form T.A.B.C. This leads to the formation of the RNA duplex B.C-2. Duplex B.C-2 is recognized and processed by Dicer to silence an mRNA "silencing target" comprising sequence regions (z)*-(x)*.

FIGS. 4 and 5 illustrate embodiments in which a detection target T interacts with and opens an initiator monomer (initiator) A, that in turn reacts with a first substrate monomer B of complex B.C-1 to open up B, that in turn reacts with a second substrate monomer C of complex B.C-1 to form an inactivator dsRNA duplex B.C-2.

In some embodiments, at least three nucleic acid (e.g., RNA or DNA) hairpin monomers are utilized as illustrated in FIG. 4. In the depicted embodiment, the monomers are denoted “A”, “B”, and “C”. In the absence of the detection target, monomers A, B, C, and the silencing target co-exist metastably. Monomers A (initiator) and B (first substrate monomer) preferably each comprise a sticky end, a hairpin loop region at the opposite end of the sticky end, and two “stems regions,” a first stem region and a second stem region, that together can form a duplex region. Monomer C (second substrate monomer) preferably comprises a hairpin loop region and two “stems regions,” a first stem region and a second stem region, that together can form a duplex region. The small letters represent sequence segments. Letters marked with an asterisk (*) are complementary to the corresponding unmarked letter.

In some embodiments, the first stem region of a monomer can hybridize to the second stem region of the monomer to form the hairpin structure. For example, as shown in FIG. 4, the monomer (A) comprises a first stem region comprising a region (v-y) that is able to hybridize to the second stem region (v*-y*). In some embodiments, in the absence of a detection target, the first and second stem regions of each monomer are hybridized to form a duplex region of the monomer.

In FIG. 4, a monomer (A) (hereinafter referred to as the “initiator”) comprises a “detection target binding region” (comprising the sequence u-v-y-s) and an “initiator region” comprising the sequence x*-y*. In the depicted embodiment, a first substrate monomer (B) comprises an “initiator complement region” x-y and a “silencing target complement region” (comprising the sequence (x*)-(z*)). In the depicted embodiment, a second substrate monomer C comprises a “silencing target region” (comprising the sequence (x)-(z)) and a “recycling region” having the same sequence as the initiator region of the initiator (comprising the sequence x*-y*).

In the depicted embodiment, monomer B comprises a region (y-(z*)) complementary to a region of monomer C (y*-(z)). As illustrated in FIG. 4, the hairpin loop region of B comprises y-(z*) and the hairpin loop region of C comprises y*-(z). This results in the formation of complex B.C-1.

The detection stage of some embodiments of triggered RNAi is depicted in FIG. 4. A region (u*-v*-y*-s*) of the detection target (T) and the detection target binding region (u-v-y-s) of the initiator (A) are typically substantially complementary. For example, the region (u*-v*-y*-s*) of the detection target (T) is able to hybridize to the detection target binding region (u-v-y-s) of the initiator (A).

The initiator (A) preferably comprises a sticky end u, which is a portion of the detection target binding region (u-v-y-s). Sticky end u of the initiator is complementary to a sequence segment u* of a detection target (T; FIG. 4). In some embodiments, the detector complement region of an initiator can comprise a sticky end and a portion of the first stem region of the initiator. For example, in the depicted figure, the initiator (A) has a detection target binding region u-v-y-s, where u is a sticky end, and v-y is portion of the first stem region of the initiator. In other embodiments, the detector complement region of an initiator can comprise a sticky end, a portion of the first stem region of the initiator, and a portion of the hairpin loop region (for example, region s in FIG. 4). Preferably, upon hybridization of the detection target to the sticky end of the detector complement region of the initiator, one arm of the hairpin structure is displaced. This opens the hairpin. In the depicted embodiment, the detection target (T) nucleates at the sticky end u of the initiator (A) by pairing segment u* with u. This induces a strand displacement interaction resulting in the hybridization of the detection target (T) at a region u*-v*-y*-s* to the detection target binding region u-v-y-s of the initiator (A) to resulting in the formation of complex T.A (step (1) in FIG. 4). In the depicted embodiment, T.A has a newly exposed single-stranded tail that contains the sequence v*-y*-x*-t.

The inactivator dsRNA formation stage of some embodiments of triggered RNAi is depicted in FIG. 4. In the depicted embodiment, the single-stranded tail of the T.A complex nucleates at the segment y in the hairpin loop region of monomer B, and induces a strand displacement interaction to open B (step (2)). The exposed region of B nucleates at the hairpin loop of C, thereby opening C. This subsequently results in the formation of duplex B.C-2 and the T.A complex is displaced from monomer B (step (3)). Complex B.C-2 comprises an inactivator dsRNA. For example, the inactivator dsRNA can be of a size that can be processed by Dicer. In the depicted embodiment, complex B.C-2 contains a 25-bp RNA duplex substrate that can be processed by dicer (Integrated DNA Technologies, 2007) in the silencing stage. However, the length of the RNA duplex substrate can vary, and will depend on the design of the substrate monomers used to form the duplex substrate. The composition of the inactivator RNAs is discussed in more detail below.

As illustrated in FIG. 5, in some embodiments, monomer B comprises an external toehold region, r, at the 5' end of monomer B which can further facilitate the reaction between complex T.A and complex B.C-1 to open B. As illustrated in FIG. 5, the single-stranded tail of the T.A complex nucleates at the segment r in the sticky end of monomer B, and induces a strand displacement interaction to open B (step (2)).

The silencing stage of some embodiments of triggered RNAi is depicted in FIG. 4. In the depicted embodiment, the RNA duplex substrate (25-bp RNA duplex substrate) of complex B.C-2 is recognized by Dicer and processed to induce RNAi action. This results in the suppression of the mRNA target sequence x-z (which is independent of the mRNA detection target u*-v*-y*-s*).

Figure 6:
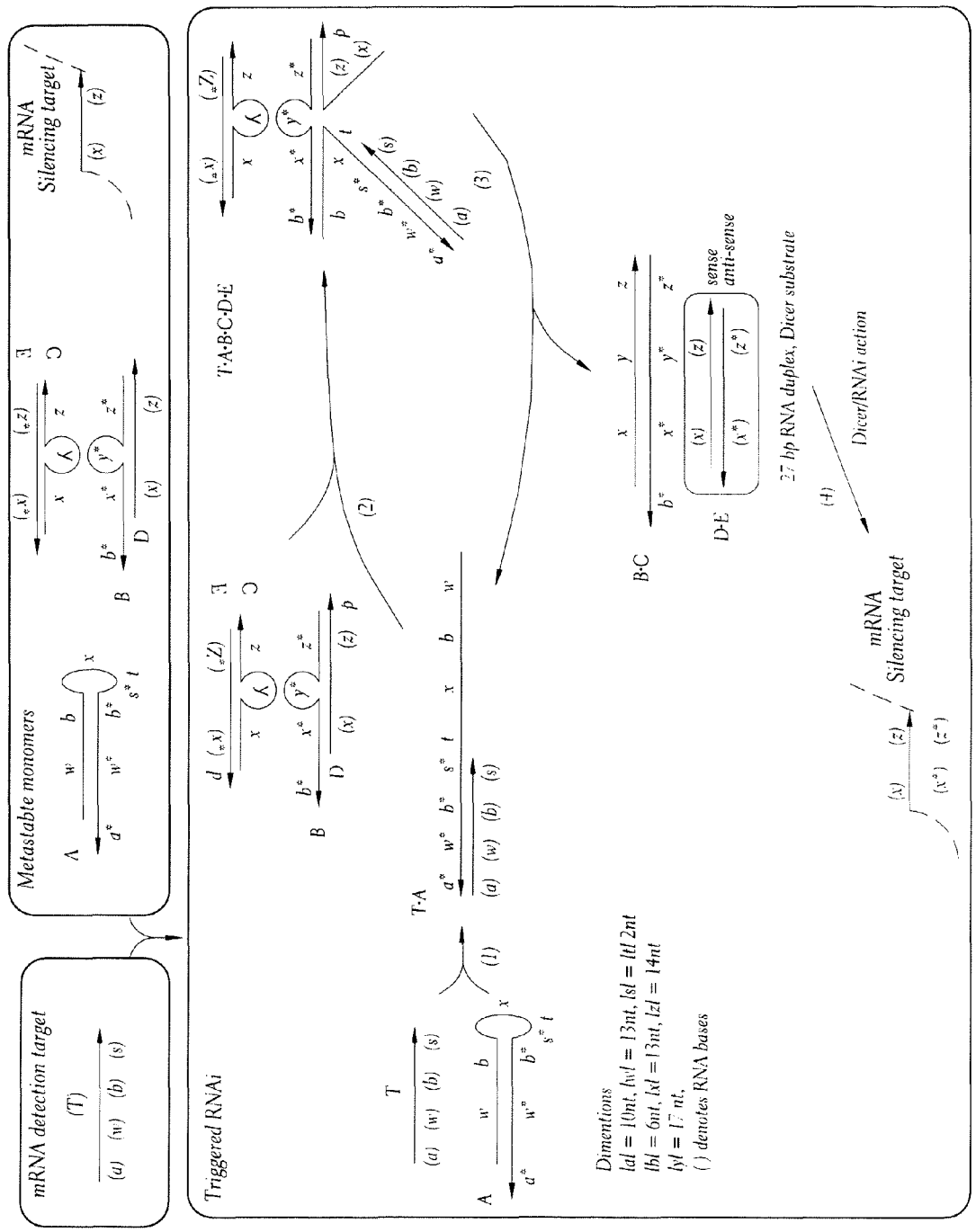
FIG. 6 schematically illustrates another embodiment of a triggered RNAi system using the five synthetic nucleic acid strands, A, B, C, D, and E, shown.

In some embodiments, one nucleic acid (e.g., RNA or DNA) hairpin monomer (A) and two nucleic acid complexes (B.D and C.E) are utilized as illustrated in FIG. 6. FIG. 6 is illustrative of embodiments in which a detection target T interacts with and opens an initiator monomer (initiator) A, that in turn reacts with a monomer (or strand) D of a first substrate complex B.D. to open up D, that in turn reacts with a monomer (or strand) E of a second substrate complex C.E to form an inactivator dsRNA duplex D.E.

Monomer A (initiator) preferably comprise a sticky end, a hairpin loop region at the opposite end of the sticky end, and two "stems regions," a first stem region and a second stem region, that together can form a duplex region. Complexes B.D and C.E each preferably comprise a bulge loop region, a first stem region, and a second stem region, that together can form a duplex. The stem regions are substantially complementary.

In FIG. 6, a monomer (A) (hereinafter referred to as the "initiator") comprises a "detection target binding region" (comprising the sequence a*-w*-b*-s*) and an "initiator region" comprising the sequence b-x. In the depicted embodiment, a first substrate complex (B.D) comprises an "initiator complement region" b*-x* and a "silencing target region" (comprising the sequence (x)-(z)). In the depicted embodiment, a second substrate complex C.E comprises a "silencing target complement region" (comprising the sequence (x*)-(z*)). Complex B.D preferably comprises nucleic acid monomers B and D. In the depicted embodiment, regions x* and z* of monomer B are complementary to regions (x) and (z) of monomer D. The monomers are associated into a complex in the absence of a target. Complex C.E preferably comprises nucleic acid monomers C and E. In the depicted embodiment, regions x and z of monomer C are complementary to regions (x*) and (z*) of monomer E. The monomers are associated into a complex in the absence of a target.

In the depicted embodiment, complex B.D comprises a bulge loop region (y*)) complementary to a bulge loop region of complex C.E (y). This results in the formation of complex D.B.C.E. In the absence of the detection target, monomer A, complex B.D, complex C.E, and the silencing target co-exist metastably.

The detection stage of some embodiments of triggered RNAi is depicted in FIG. 6. A region ((a)-(w)-(b)-(s)) of the detection target (T) and the detection target binding region (a*-w*-b*-s*) of the initiator (A) are typically substantially complementary. For example, the region ((a)-(w)-(b)-(s)) of the detection target (T) is able to hybridize to the detection target binding region (a*-w*-b*-s*) of the initiator (A).

The initiator (A) preferably comprises a sticky end a*, which is a portion of the detection target binding region (a*-w*-b*-s*). Sticky end a* of the initiator is complementary to a sequence segment a of a detection target (T; FIG. 6). In some embodiments, the detector complement region of an initiator can comprise a sticky end and a portion of the first stem region of the initiator. For example, in the depicted figure, the initiator (A) has a detection target binding region (a*-w*-b*-s*), where a* is a sticky end, and w*-b* is portion of the first stem region of the initiator. In other embodiments, the detector complement region of an initiator can comprise a sticky end, a portion of the first stem region of the initiator, and a portion of the hairpin loop region (for example, region s* in FIG. 6). Preferably, upon hybridization of the detection target to the sticky end of the detector complement region of the initiator, one arm of the hairpin structure is displaced. This opens the hairpin. In the depicted embodiment, the detection target (T) nucleates at the sticky end a* of the initiator (A) by pairing segment a with a*. This induces a strand displacement interaction resulting in the hybridization of the detection target (T) at a region ((a)-(w)-(b)-(s)) to the detection target binding region a*-w*-b*-s* of the initiator (A) to resulting in the formation of complex T.A (step (1) in FIG. 6). In the depicted embodiment, T.A has a newly exposed single-stranded tail that contains the sequence w-b-x-t.

The inactivator dsRNA formation stage of some embodiments of triggered RNAi is depicted in FIG. 6. In the depicted embodiment, the single-stranded tail of the T.A complex nucleates at the segment b* on monomer B and partially displaces monomer D from monomer B (step (2)). This subsequently results in the formation of duplex B.C and duplex D.E, and the T.A complex is displaced from monomer B (step (3)). Complex D.E comprises an inactivator dsRNA. For example, the inactivator dsRNA can be of a size that can be processed by Dicer. In the depicted embodiment, complex D.E contains a 27-bp RNA duplex substrate that can be processed by dicer (Integrated DNA Technologies, 2007) in the silencing stage. However, the length of the RNA duplex substrate can vary, and will depend on the design of the substrate monomers used to form the duplex substrate. The composition of the inactivator RNAs is discussed in more detail below.

Figure 9:
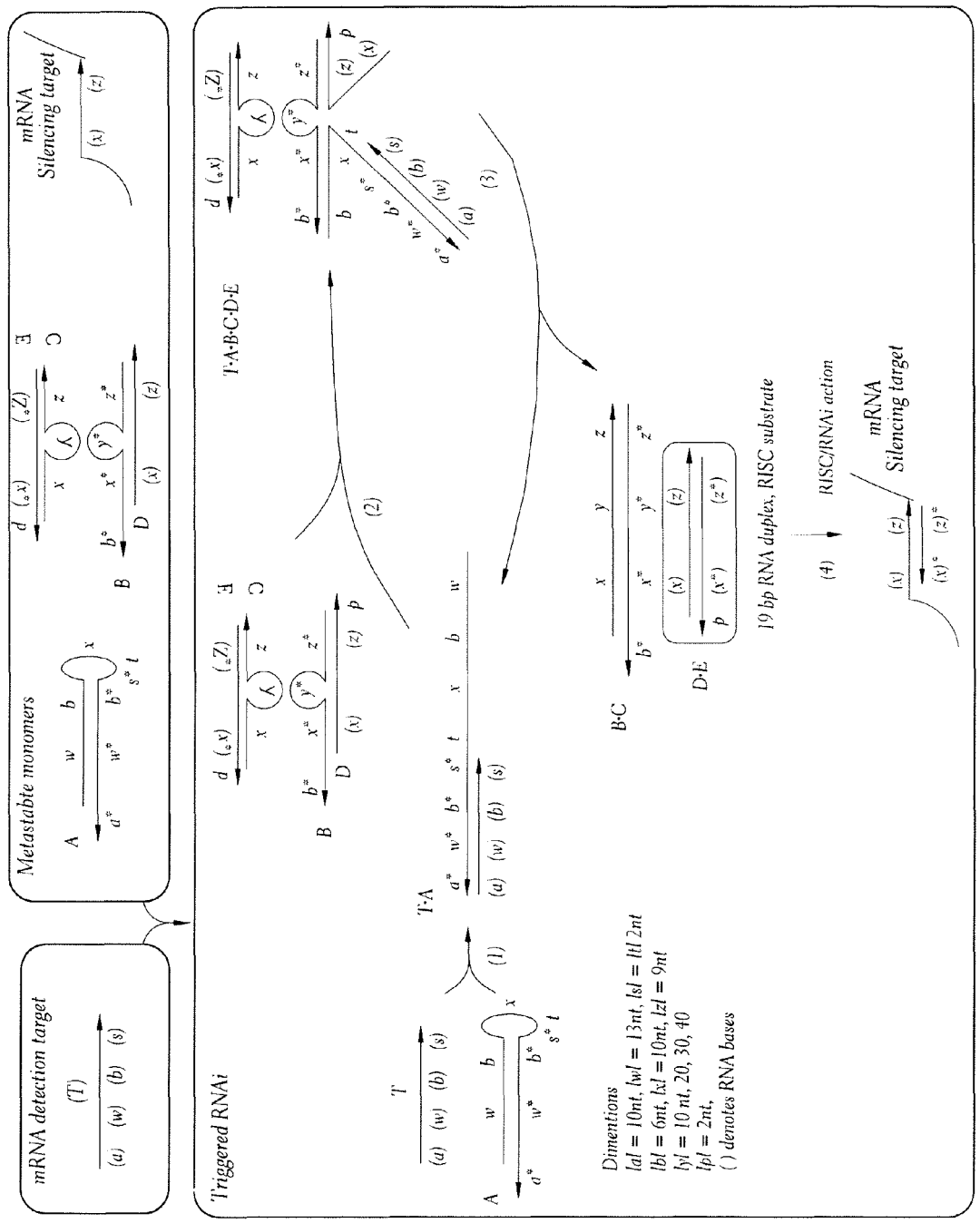
FIG. 9 schematically illustrates another embodiment of a triggered RNAi system. There are five synthetic nucleic acid strands, A, B, C, D, and E, shown. In the absence of the mRNA "detection target" T, hairpin A, complex C.E and complex B.D co-exist metastably and do not induce RNAi action on their own. The bulge loops on C.E and B.D possess regions (y and y*, respectively) that are complementary to one another. T comprises sequence regions (a)-(w)-(b)-(s). When T is present in the system, it interacts with A to form the complex T.A. T.A, in turn, reacts with C.E and B.D to form T.A.B.C.D.E. This leads to the formation of the RNA duplexes B.C and D.E. Duplex D.E serves as siRNA which results in the silencing of an mRNA "silencing target" comprising sequence regions (x)-(z).

The silencing stage of some embodiments of triggered RNAi is depicted in FIG. 6. In the depicted embodiment, the RNA duplex substrate (27-bp RNA duplex substrate) of complex D.E is recognized by Dicer and processed to induce RNAi action. This results in the suppression of the mRNA target sequence x-z (which is independent of the mRNA detection target a-w-b-s). In some embodiments, different dimensions of the segments can be utilized (FIG. 9). The different dimensions of the segment results in the catalytic formation of a 19 bp RNA duplex that serves as siRNA at the end of step (3), which results in the silencing of the silencing target in step (4) (FIG. 9).

Figure 7:
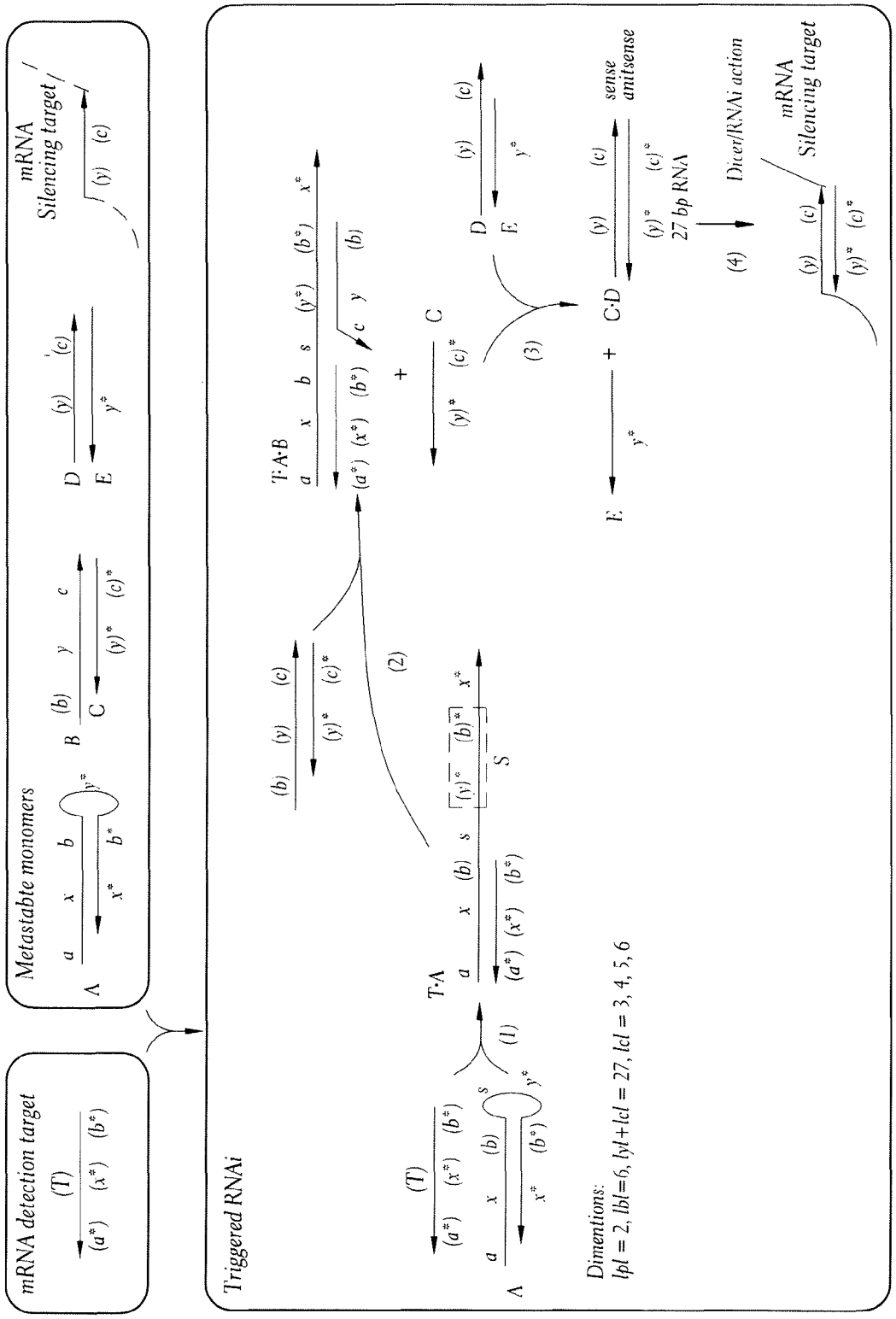
FIG. 7 schematically illustrates another embodiment of a triggered RNAi system. There are five synthetic nucleic acid strands, A, B, C, D, and E, shown. In the absence of the mRNA "detection target" T, hairpin A, complex B.C, and complex D.E co-exist metastably and do not induce RNAi action on their own. T comprises sequence regions (a*)-(x*)-(b*). When T is present in the system, it interacts with A to form the complex T.A. T.A, in turn, reacts with B.C to form T.A.B and C. C is now available to react with D.E to form E and the duplex C.D. Duplex C.D is recognized and processed by Dicer to silence an mRNA "silencing target" comprising sequence regions (y)-(c).

In some embodiments, one nucleic acid (e.g., RNA or DNA) hairpin monomer (A) and two nucleic acid complexes (B.C and D.E) are utilized as illustrated in FIG. 7. FIG. 7 is illustrative of embodiments in which a detection target T interacts with and opens an initiator monomer (initiator) A, that in turn reacts with a monomer (or strand) B of a first substrate complex B.C to displace C, that in turn reacts with a monomer (or strand) D of a second substrate complex D.E to form an inactivator dsRNA duplex C.D.

Monomer A (initiator) preferably comprise a sticky end, a hairpin loop region at the opposite end of the sticky end, and two "stems regions," a first stem region and a second stem region, that together can form a duplex region. Complex B.C preferably comprises a first stem region and a second stem region that together can form a duplex. Complex D.E preferably comprises a first stem region that can form a duplex. In FIG. 7, a monomer (A) (hereinafter referred to as the "initiator") comprises a "detection target binding region" (comprising the sequence a-x-b) and an "initiator region" comprising the sequence (b)-y. In the depicted embodiment, a first substrate complex (B.C) comprises an "initiator complement region" b*-x* and a "silencing target complement region" (comprising the sequence (y)*-(c)*). In the depicted embodiment, a second substrate complex D.E comprises a "silencing target region" (comprising the sequence (y)-(c)). Complex B.C preferably comprises nucleic acid monomers B and C. In the depicted embodiment, regions y and c of monomer B are complementary to regions (y)* and (c)* of monomer C. Complex D.E preferably comprises nucleic acid monomers D and E. In the depicted embodiment, region (y) of monomer D is complementary to regions y* of monomer E.

In the absence of the detection target, monomer A, complex B.C, complex D.E, and the silencing target co-exist metastably.

The detection stage of some embodiments of triggered RNAi is depicted in FIG. 7. A region ((a*)-(x*)-(b*)) of the detection target (T) and the detection target binding region (a-x-b) of the initiator (A) are typically substantially complementary. For example, the region ((a*)-(x*)-(b*)) of the detection target (T) is able to hybridize to the detection target binding region (a-x-b) of the initiator (A).

The initiator (A) preferably comprises a sticky end a, which is a portion of the detection target binding region (a-x-b). Sticky end a of the initiator is complementary to a sequence segment a of a detection target (T; FIG. 7). In some embodiments, the detector complement region of an initiator can comprise a sticky end and a portion of the first stem region of the initiator. For example, in the depicted figure, the initiator (A) has a detection target binding region (a-x-b), where a is a sticky end, and x-b is portion of the first stem region of the initiator. Preferably, upon hybridization of the detection target to the sticky end of the detector complement region of the initiator, one arm of the hairpin structure is displaced. This opens the hairpin. In the depicted embodiment, the detection target (T) nucleates at the sticky end a of the initiator (A) by pairing segment a* with a. This induces a strand displacement interaction resulting in the hybridization of the detection target (T) at a region ((a*)-(x*)-(b*)) to the detection target binding region (a-x-b) of the initiator (A) to resulting in the formation of complex T.A (step (1) in FIG. 7). In the depicted embodiment, T.A has a newly exposed single-stranded tail that contains the sequence s-y*-b*-x*.

The inactivator dsRNA formation stage of some embodiments of triggered RNAi is depicted in FIG. 7. In the depicted embodiment, the single-stranded tail of the T.A complex nucleates at the segment b on monomer B and displaces monomer C from monomer B (step (2)). The displaced monomer C further nucleates at the segment c of the D.E complex and displaces monomer E from monomer D, resulting in the duplex C.D (step (3)). Complex C.D comprises an inactivator dsRNA. For example, the inactivator dsRNA can be of a size that can be processed by Dicer. In the depicted embodiment, complex C.D contains a 27-bp RNA duplex substrate that can be processed by dicer (Integrated DNA Technologies, 2007) in the silencing stage. However, the length of the RNA duplex substrate can vary, and will depend on the design of the substrate monomers used to form the duplex substrate. The composition of the inactivator RNAs is discussed in more detail below.

Figure 10:
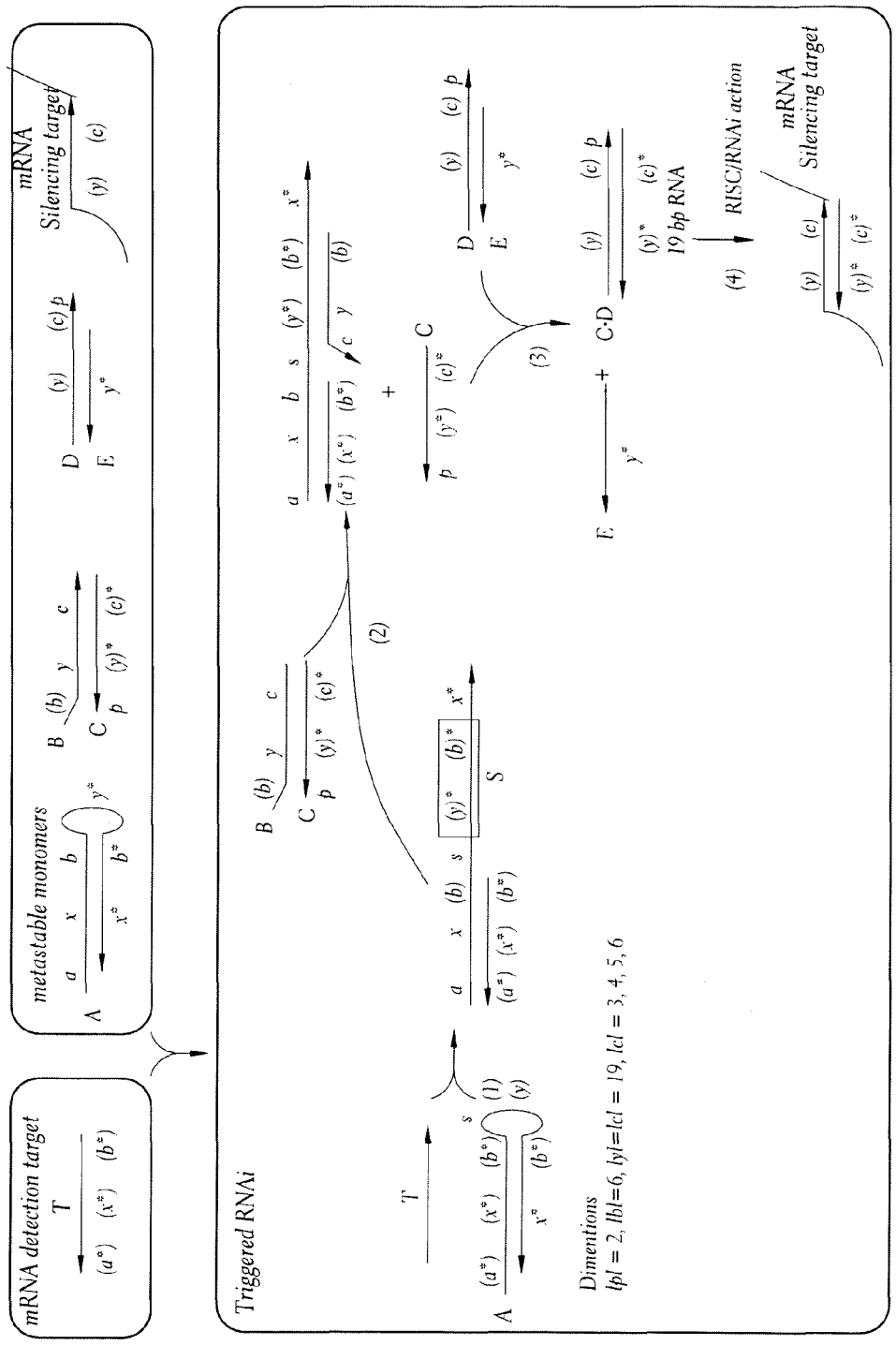
FIG. 10 schematically illustrates another embodiment of a triggered RNAi system. There are five synthetic nucleic acid strands, A, B, C, D, and E, shown. In the absence of the mRNA "detection target" T, hairpin A, complex B.C, and complex D.E co-exist metastably and do not induce RNAi action on their own. T comprises sequence regions (a*)-(x*)-(b*). When T is present in the system, it interacts with A to form the complex T.A. T.A, in turn, reacts with B.C to form T.A.B and C. C is now available to react with D.E to form E and the duplex C.D. Duplex C.D serves as siRNA which results in the silencing of an mRNA "silencing target" comprising sequence regions (y)-(c).

The silencing stage of some embodiments of triggered RNAi is depicted in FIG. 7. In the depicted embodiment, the RNA duplex substrate (27-bp RNA duplex substrate) of complex C.D is recognized by Dicer and processed to induce RNAi action. This results in the suppression of the mRNA target sequence y-c (which is independent of the mRNA detection target b*-x*-a*). In some embodiments, different dimensions of the segments can be utilized (FIG. 10). the different dimensions of the segment results in the catalytic formation of a 19 bp RNA duplex that serves as siRNA at the end of step (3), which results in the silencing of the silencing target in step (4) (FIG. 10).

Figure 8:
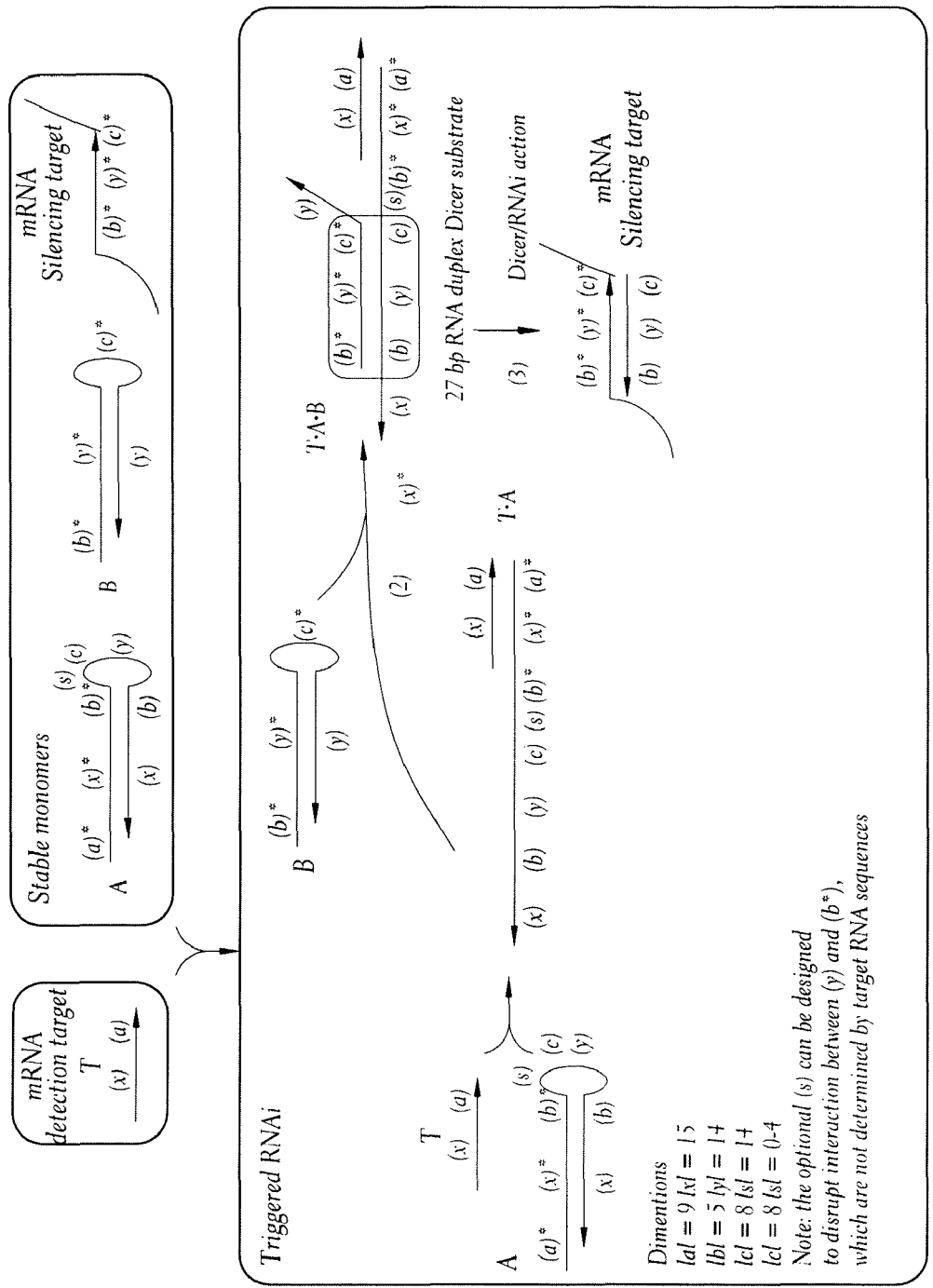
FIG. 8 schematically illustrates another embodiment of a triggered RNAi system. There are 2 synthetic nucleic acid hairpin strands, A and B, shown. In the absence of the mRNA "detection target" T, hairpin A, and hairpin B co-exist stably and do not induce RNAi action on their own. T comprises sequence regions (x)-(a). When T is present in the system, it interacts with A to form the complex T.A. T.A, in turn, reacts with B to form T.A.B. T.A.B is recognized and processed by Dicer to silence an mRNA "silencing target" comprising sequence regions (b)*-(y)*-(c)*.

In some embodiments, at least two nucleic acid (e.g., RNA or DNA) hairpin monomers are utilized as illustrated in FIG. 8. In the depicted embodiment, the monomers are denoted "A" and "B". In the absence of the detection target, monomer A, monomer B, and the silencing target co-exist stably. FIG. 8 is illustrative of embodiments in which a detection target T interacts with and opens an initiator monomer (initiator) A, that in turn reacts with a first substrate monomer B to form an inactivator dsRNA duplex T.A.B.

Monomers A (initiator) preferably comprises a sticky end, a hairpin loop region at the opposite end of the sticky end, and two "stems regions," a first stem region and a second stem region, that together can form a duplex region. Monomer B (substrate monomer) preferably comprises a sticky end, a hairpin loop region at the opposite end of the sticky end, and one "stems region" that can form a duplex region.

In FIG. 8, a monomer (A) (hereinafter referred to as the "initiator") comprises a "detection target binding region" (comprising the sequence (a)*-(x)*), an "initiator region" (comprising the sequence (b)-(y)-(c)), and a "silencing target complement region" (comprising the sequence (b)-(y)-(c)). In the depicted embodiment, the initiator region and the silencing target complement region comprise identical sequences. In some embodiments, the initiator region and the silencing target complement region comprise substantially identical sequences. In the depicted embodiment, a substrate monomer B comprises an "initiator complement region" (comprising the sequence (b)*-(y)*-(c)*) and a "silencing target region" (comprising the sequence (b)*-(y)*-(c)*). In the depicted embodiment, the initiator complement region and the silencing target region comprise identical sequences. In some embodiments, the initiator complement region and the silencing target region comprise substantially identical sequences.

The detection stage of some embodiments of triggered RNAi is depicted in FIG. 8. A region ((x)-(a)) of the detection target (T) and the detection target binding region ((a)*-(x)*) of the initiator (A) are typically substantially complementary. For example, the region ((x)-(a)) of the detection target (T) is able to hybridize to the detection target binding region ((a)*-(x)*) of the initiator (A).

The initiator (A) preferably comprises a sticky end (a)*, which is a portion of the detection target binding region ((a)*-(x)*). Sticky end (a)* of the initiator is complementary to a sequence segment (a) of a detection target (T; FIG. 8). In some embodiments, the detector complement region of an initiator can comprise a sticky end and a portion of the first stem region of the initiator. For example, in the depicted figure, the initiator (A) has a detection target binding region (a)*-(x)*, where (a)* is a sticky end, and (x)* is portion of the first stem region of the initiator Preferably, upon hybridization of the detection target to the sticky end of the detector complement region of the initiator, one arm of the hairpin structure is displaced. This opens the hairpin. In the depicted embodiment, the detection target (T) nucleates at the sticky end (a)* of the initiator (A) by pairing segment (a) with (a)*. This induces a strand displacement interaction resulting in the hybridization of the detection target (T) at a region (x)-(a) to the detection target binding region (a)*-(x)* of the initiator (A) to resulting in the formation of complex T.A (step (I) in FIG. 8). In the depicted embodiment, T.A has a newly exposed single-stranded tail that contains the sequence b*-s-c-y-b-x.

The inactivator dsRNA formation stage of some embodiments of triggered RNAi is depicted in FIG. 8. In the depicted embodiment, the single-stranded tail of the T.A complex nucleates at the segment b* on monomer B and opens monomer B (step (2)). This subsequently results in the formation of complex T.A.B (step (2)). Complex T.A.B comprises an inactivator dsRNA. For example, the inactivator dsRNA can be of a size that can be processed by Dicer. In the depicted embodiment, complex T.A.B contains a 27-bp RNA duplex substrate that can be processed by dicer (Integrated DNA Technologies, 2007) in the silencing stage. However, the length of the RNA duplex substrate can vary, and will depend on the design of the substrate monomers used to form the duplex substrate. The composition of the inactivator RNAs is discussed in more detail below.

The silencing stage of some embodiments of triggered RNAi is depicted in FIG. 8. In the depicted embodiment, the RNA duplex substrate (27-bp RNA duplex substrate) of complex T.A.B is recognized by Dicer and processed to induce RNAi action. This results in the suppression of the mRNA target sequence (b)*-(y)*-(c)* (which is independent of the mRNA detection target (x)-(a)).

The mRNA silencing target sequence can be a portion of the sequence of any gene for which silencing is desirable in the presence of the detection target. The silencing target can be a sequence which may or may not be associated with a disease or disorder. Silencing targets are discussed in detail below.

In some embodiments, the result is an RNA duplex comprising an inactivator dsRNA. In some embodiments, the inactivator dsRNA can comprise an RNA duplex substrate that can be processed by Dicer. Dicer processing of the RNA duplex substrate produces small interfering RNAs (siRNAs). The siRNAs can then be processed by the RISC complex, which unwinds the siRNA and retains one strand as a targeting co-factor. The RISC-siRNA complex recognizes and induces the degradation of the silencing target mRNA, which is complementary to the siRNA strand retained by the RISC complex.

The length of the hairpin loop, stem regions and sticky ends of the monomers can be adjusted, for example to ensure kinetic stability in particular reaction conditions and to adjust the rate of polymerization in the presence of initiator. In some embodiments the length of the sticky ends is the same as the length of the hairpin loops. In other embodiments the sticky ends are longer or shorter than the hairpin loops. In some embodiments, if the hairpin loops are longer than the sticky ends, the hairpin loops can comprise a region that is complementary to the sticky end of a monomer.

In some embodiments the length of the hairpin loops is short relative to the stems. For example, the stems may be two or three times as long as the hairpin loops.

The loop regions are preferably between about 1 and about 100 nucleotides, and more preferably between about 3 and about 30 nucleotides. In one embodiment the loops and sticky ends of a pair of hairpin monomers are about 6 nucleotides in length and the stems are about 18 nucleotides long.

The regions (e.g., a, b, c, x, y and z) are not limited to any particular sequences or number of bases, and are designed based on the particular detection and silencing targets of the triggered RNAi reaction. For example, in FIGS. 2 and 3, sample segment lengths expressed as numbers of bases can be, for example without limitation, a=7, b=7, c=7, x=8, y=8, and z=12. Sample compositions (RNA or DNA) for segments of the first, second and third monomers (A, B and C) can be, for example without limitation: A: a-x-b-y*-c*-b*-x*; B: b-c-y-b*-(z*-y*-c*); C: (c-y-z)-b-y*-c*-b*-z*-y*, where RNA segments are contained inside parentheses and DNA segments are not contained inside parenthesis. For example, in FIG. 4, sample segment lengths expressed as numbers of bases can be, for example without limitation, u=10, v=10, y=10, s=2, t=2, and p=2, x-z=13-12 or 15-10 or 16-9. For example, in FIG. 5, sample segment lengths expressed as numbers of bases can be, for example without limitation, r=6, and p=2, x-y-z=10-15-7 or 14-11-3 or 16-9-1. For example, in FIG. 6, sample segment lengths expressed as numbers of bases can be, for example without limitation, a=10, w=13, y=10, s=2, t=2, b=6, x=13, z=14, and y=17. For example, in FIG. 7, sample segment lengths expressed as numbers of bases can be, for example without limitation, p=2, b=6, y+c=27, and c=3, 4, 5, or 6. For example, in FIG. 8, sample segment lengths expressed as numbers of bases can be, for example without limitation, a=9, b=5, c=8, x=15, y=14, and s=0, 1, 2, 3, or 4. The segment (s) is optional and can be designed to disrupt the interaction between (y) and (b*), which are not determined by target RNA sequences. For example, in FIG. 9, sample segment lengths expressed as numbers of bases can be, for example without limitation, a=10, w=13, s=2, t=2, b=6, x=10, z=9, y=10, 20, 30, or 40, and p=2. For example, in FIG. 9, sample segment lengths expressed as numbers of bases can be, for example without limitation, p=2, b=6, y+c=19, c=3, 4, 5, or 6.

Other refinements to the system stabilize the monomer hairpins to help prevent triggered RNAi in the absence of an activated initiator. This can be achieved, for example, via super-stable hairpin loop sequences (Nakano et al. *Biochemistry* 41:14281-14292 (2002), herein incorporated by reference in its entirety), with ostensible structural features that could further inhibit direct hybridization to the hairpin. In other embodiments hairpin loops are made to be self-complementary at their ends. This self-complementation "pinches" the hairpin loops, making them shorter. However, if the reactive sticky ends of each monomer are complementary to the loop regions on the opposite monomer, as described above, they will have a slight propensity to close up, thereby slowing down the reaction. This feature can be utilized if a slower reaction is desired. Completely self-complementary hairpins can also be used, for example if the monomer hairpins are forming dimers with interior loops that are more easily invaded than their hairpin counterparts.

Reaction conditions are preferably selected such that hybridization is able to occur, including between the detection target and the sticky end of an initiator, between the initiator region of an initiator and a sticky end of a first monomer, between the silencing target complement region of a first monomer and the sticky end of a second monomer, between the first and second stem regions of the monomers themselves, and between monomers that comprise a complex. At each step of monomer polymerization, energy is gained from the hybridization of the sticky end of the monomer. The reaction temperature does not need to be changed to facilitate the polymerization of triggered RNAi monomers. That is, the triggered RNAi monomer polymerization reactions are isothermic. They also do not require the presence of any enzymes. However, in some embodiments, Dicer is used to process the dsRNA substrate produced by polymerization of the monomers. In some embodiments, the RISC complex is used to unwind the siRNA and induce the degradation of the silencing target mRNA, which is complementary to the siRNA strand retained by the RISC complex.

Detection Targets

The detection target is preferably a nucleic acid or other molecule that is able to contact the initiator and trigger RNAi through the formation of an inactivator dsRNA. The detection target can comprise, but is not limited to, any of the following: a nucleic acid sequence, a peptide, a polypeptide, an antibody or fragment thereof, a signal cascade molecule, a lipid, a carbohydrate, a fused entity, a viral particle, a bacterium or a parasitic organism. In some embodiments, the detection target can be a portion of a nucleic acid associated with a disease or disorder.

In some embodiments the detection target is preferably a nucleic acid molecule. The nucleic acid detection target comprises a sequence that is complementary to a portion, such as, for example, a sticky end, of an initiator that is available for hybridization with the detection target while the initiator is in its kinetically stable state. The detection target also preferably comprises a sequence that is complementary to a portion of the initiator adjacent to the sticky end such that hybridization of the detection target to the sticky end causes a conformational change in the initiator and begins the triggered RNAi reaction. For example, the detection target may comprise a region that is complementary to the detection target binding region of the initiator, as described above and illustrated in FIG. 2A.

In some embodiments, the detection target binding region of the initiator is preferably at least 80%, more preferably at least 90%, 95% or higher, identical to at least a portion of detection target. In preferred embodiments, the detection target binding region is at least 2, 3, 4, 5, or 10 or more bases in length.

In various embodiments, the detection target can be, for example, a protein, a carbohydrate, a fatty acid, a hormone, or a polynucleotide. The detection target can be an entire molecule or a portion of any molecule in whose presence, marker or reporter gene expression is modulated. In some embodiments, the detection target can be a nucleic acid sequence. In some embodiments, the detection target can be at least a portion of the sequence of any gene for which silencing is desirable in the presence of the detection target. In some embodiments, the detection target can be an mRNA. In other embodiments, the detection target can be DNA. The detection target can be a sequence which may or may not be associated with a disease or disorder.

In some embodiments, detection target can be a molecule (e.g., a nucleic acid) or a portion of a molecule associated with a pathogen. In some embodiments, the detection target can be a nucleic acid, or a portion of a nucleic acid sequence that is necessary for the life cycle or replication of a virus, such as, for example, gene expression of the virus and the expression of a cellular receptor or co-receptor necessary for viral replication. In some particular embodiment of the invention, the virus is the human immunodeficiency virus (HIV). The detection target sequence may be, for example, selected from the group consisting of Rev, Gag, Pol, LTRs, TAR, RRE, att, pbs, ppt and other essential DNA and RNA cis-regulatory elements. In one embodiment of the invention, the detection target is an expressed region of the HIV viral genome, for example, a portion of the 9-kb transcript of the integrated HIV virus, or any of the variously spliced mRNA transcripts of HIV (Schwartz, S; Felber, B K; Benko, D M; Fenya, E M; Pavlakis, G N. Cloning and functional analysis of multiply spliced mRNA species of human immunodeficiency virus type 1. *J. Virol.* 1990; 64(6): 2519-29). Target regions within the HIV transcripts can be chosen to correspond to any of the viral genes, including, for example, HIV-1 LTR, vif, nef and rev.

In some embodiments, the detection target can be a sequence that is necessary for the life cycle or replication of a tumor cell. In other embodiments, the detection target can be a sequence that is indicative of a pre-cancerous state, such as, for example, an oncogene sequence. In some embodiments, the detection target can be a PKR sequence. In some embodiments, the detection target can be a marker such as a molecule associated with a specific cell type.

Silencing Targets

In preferred embodiments, the silencing target can be an mRNA. In various embodiments, the silencing target can be a nucleic acid sequence. In various embodiments, the silencing target can comprise at least a portion of the nucleic acid sequence of any gene for which silencing is desirable in the presence of the detection target. The silencing target can be a nucleic acid sequence which may or may not be associated with a disease or disorder. In some embodiments, the silencing target can be a nucleic acid of at least a portion of a gene. In some embodiments, the silencing target can be an a nucleic acid of at least a portion of an endogenous gene. In other embodiments, the silencing target can be an nucleic acid of at least a portion of an exogenous gene.

In some embodiments, the silencing target can comprise a marker or reporter gene. Marker or reporter genes are known in the art, such as, for example, GFP and other imaging or diagnostic markers. The detection of a detection target of interest can thus result in a change of, for example, the fluorescence emission of GFP via triggered RNAi.

In some embodiments, the silencing target gene can encode a protein that modulates the expression of a marker or reporter gene. Such silencing target genes include, but are not limited to, transcription factors, repressors, activators, and enhancers (see, for example, Elowitz M B et al. Nature. 2000 Jan. 20; 403(6767):335-8, which is herein incorporated by reference in its entirety). For example, suitable repressors include, but are not limited to, LacI, tetR, and cI. In some embodiments, the silencing target gene can encode a ribosomal protein. In some embodiments, the silencing target gene can encode an enzyme involved in protein degradation such as, for example, a ubiquitin activating enzyme or a ubiquitin-conjugating enzyme. In some embodiments, the gene can encode a kinase, such as, for example, protein kinase C. In some embodiments, the silencing target gene can encode, for example, any gene that can encode a transcription factor. In some embodiments, the silencing target gene can encode a polymerase, such as RNA polymerase I.

In some embodiments, the silencing target gene can regulate (e.g., by binding) one or more regulatory elements of the naturally occurring marker gene. In other embodiments, the silencing target gene can regulate elements not normally associated with the marker gene. For example, the coding region of the marker gene or a portion of the marker gene can be placed under the control of one or more non-naturally occurring regulatory elements (e.g., synthetic regulatory sequences, minimal promoter sequences, and regulatory and/or promoter sequences from other genes) using methods known in the art, such as recombinant DNA technology. In this way, one of skill in the art can determine the silencing target gene that can be used to modulate the marker or reporter molecule. In some embodiments, the silencing target gene is at least a portion of an endogenous gene. In other embodiments, the silencing target gene is at least a portion of an exogenous gene.

Marker or Reporter Molecule

In some embodiments, the marker can be a nucleic acid sequence (e.g., a gene). In various embodiments, the marker can comprise at least a portion of the nucleic acid sequence of any gene for which detection is desirable in the presence of the detection target. In some embodiments, the marker can comprise any protein or fragment thereof that can be detected. In various embodiments, the marker can encode a gene that can be readily visualized (e.g., by fluorescence emission). In some embodiments, the markers are genes encoding fluorescent proteins. Suitable fluorescent markers include, but are not limited to, GFP, blue fluorescent protein (BFP), yellow fluorescent protein, red fluorescent protein (RFP), cyan fluorescent protein (CFP), and derivatives and mutants thereof. A marker gene can comprise any marker or reporter molecule known in the art (see, for example, M. Zimmer. Glowing Genes: A Revolution In Biotechnology. Buffalo, N.Y.: Prometheus Book, 2005, which is herein incorporated by reference in its entirety). Detection of fluorescence can be carried out by any method known in the art, including, but not limited to, fluorescence microscopy, single- or multiple-photon microscopy, time-resolved fluorescence microscopy and fluorescence endoscopy. In some embodiments, the marker gene can comprise any gene or encode any protein that can be readily detected by methods known in the art (e.g., luciferase or beta-galactosidase).

The term "detect" or "measure" refers to identifying the presence, absence, amount, or level of the object to be detected (for example, a marker such as GFP). As used herein, the term "level" refers to the level of fluorescence of a marker or the expression levels of RNA, protein, or to DNA copy number of a marker. Typically, the level of the marker in a sample obtained from the subject is different (for example, increased or decreased) from a predetermined level (for example, the level of the same variant in a similar sample obtained from a healthy individual).

As used herein, "predetermined level" refers to the level of expression of a marker or in a control sample (e.g., a biological sample from a subject without a disease or disorder). In some embodiments, the detection target can be detected by assessing whether the marker expression varies from a predetermined level. For instance, the difference may be greater than, less than, equal to, or any number in between about 5%, 10%, 15%, 20%, 25%, 30%, 35%, 40%, 45%, 50%, 55%, 60%, 65%, 70%, 75%, 80%, 85%, 90%, 95%, 100%, 110%, 125%, 150%, 175%, 200%, 250%, 300%, 350%, 400%, 450%, 500%, 550%, 600%, 650%, 700%, 750%, 800%, 850%, 900%, 950%, 1000%, 5000%, 10000%, 100000% or greater. The predetermined level can be determined from a control. The control can also be a standard or known amount of a reference marker (for example, GFP). For example, the predetermined level can be the level of fluorescence of the marker (e.g., GFP) in the absence of the initiator.

The term "about" or "approximately" means within an acceptable error range for the particular value as determined by one of ordinary skill in the art, which will depend in part on how the value is measured or determined, for example, the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

A sample can be any source for which it is desirable to detect a detection target by modulating the expression of a marker or reporter molecule. In some embodiments, the sample is a biological sample. Biological samples include, for example, cells, blood, serum, plasma, urine, lymph, tissue and products thereof. Samples can be obtained by any method known in the art. Methods for obtaining a biological sample include, but are not limited to, fluid collection, fine needle biopsy, needle biopsy, core needle biopsy and surgical biopsy (for example, brain biopsy), lavage, and any known method in the art. Regardless of the procedure employed, once a sample is obtained, the level of the marker can be determined.

Diseases

Embodiments disclosed herein relate to diagnostic and prognostic methods for the detection of a disease or disorder and/or monitoring the progression of a disease or disorder. As used herein, the phrase "diagnostic" refers identifying the presence of or nature of a disease or disorder. The detection of a detection target by determining the level of expression of one or more markers or reporters (e.g., GFP) provides a means of diagnosing the disease or disorder. Such detection methods may be used, for example, for early diagnosis of the condition, to determine whether a subject is predisposed to a disease or disorder, to monitor the progress of the disease or disorder or the progress of treatment protocols, to assess the severity of the disease or disorder, to forecast the an outcome of a disease or disorder and/or prospects of recovery, or to aid in the determination of a suitable treatment for a subject. The detection can occur in vitro or in vivo. In some embodiments, the methods described herein can be used in vivo. Some embodiments described herein provide for detection methods that are desirable for in vivo applications because specific detection of the detection target can occur even if the marker gene is provided to a mixture of cells that include cells in which the detection target is absent and cells in which the detection target is present.

In some embodiments, the disease or disorder can be diagnosed by assessing whether the marker expression varies from a predetermined level. The predetermined level can be determined from a control. A control can be a sample or its equivalent from a normal patient or from a patient in a known disease state.

Diseases contemplated for diagnosis in embodiments described herein include any disease in which a detection target, such as a target associated with the disease is present in a cell and can initiate polymerization of triggered RNAi hairpin monomers. The detection target can act on an initiator to trigger formation of RNA duplex substrates for RNAi machinery such as Dicer. Preferred embodiments include, but are not limited to, diseases in which the detection target is a nucleic acid molecule. In some embodiments, the nucleic acid molecule is an mRNA molecule associated with a disease or disorder, such as a mutant mRNA molecule. However, disease-associated RNAi detection targets can be, for example and without limitation, nucleic acid sequences, proteins, peptides, lipids, carbohydrates and small molecules.

In some embodiments, the disease to be diagnosed is a type of cancer, such as, for example, leukemia, carcinoma, lymphoma, astrocytoma, sarcoma and particularly Ewing's sarcoma, glioma, retinoblastoma, melanoma, Wilm's tumor, bladder cancer, breast cancer, colon cancer, hepatocellular cancer, pancreatic cancer, prostate cancer, lung cancer, liver cancer, stomach cancer, cervical cancer, testicular cancer, renal cell cancer, and brain cancer.

In other embodiments, the disease to be diagnosed is associated with infection by an intracellular parasite. For example, the intracellular parasite may be a virus such as, for example, an adenovirus, cytomegalovirus, Epstein-Barr virus, herpes simplex virus, human herpesvirus 6, varicella-zoster virus, hepatitis viruses, papilloma virus, parvovirus, polyomavirus, measles virus, rubella virus, human immunodeficiency virus (HIV), or human T cell leukemia virus. In other embodiments, the intracellular parasite may be a bacterium, protozoan, fungus, or a prion. More particularly, the intracellular parasite can be, for example, *Chlamydia, Listeria, Salmonella, Legionella, Brucella, Coxiella, Rickettsia, Mycobacterium, Leishmania, Trypanasoma, Toxoplasma,* and *Plasmodium*. The detection target can be any molecule (e.g., nucleic acids (e.g., genes), proteins, carbohydrates (e.g., glycosylation patterns), lipids) associated with a pathogen, such as a parasite.

Some embodiments involve methods of diagnosing a patient suffering from a disease or disorder such as, for example, a cancer, autoimmune diseases (e.g, type 1 diabetes and multiple sclerosis), or a viral infection. For example, in some embodiments, the detection of oncogenic mRNA mutations in cancer cells is triggered. Genetic fusions are common somatic oncogenic mutations and can provide suitable targets for detection and diagnosis. For example, the Philadelphia chromosome, arising from a BCR-ABL fusion, has been established as the unique cause of chronic myeloid leukemia (CML). Other conserved oncogenic fusions are found, for example, in EGFR and in EWS. Single point mutations that lead to activation of an oncogene and single point mutations that inactivate a tumor suppressor are examples of additional diagnostic targets. One example of an oncogenic single point mutation is the $BRAF^{T1799A}$ mutation (V600E), found in approximately 6.4% of all human tumors. In some embodiments, the detection target binding region is substantially complementary to a detection target region of a nucleic acid or other molecule that is associated with the disease.

Embodiments disclosed herein can also be used, for example, to diagnose autoimmune diseases (e.g, type 1 diabetes and multiple sclerosis). For example, the destruction of insulin-producing cells in diabetes and the destruction of myelin sheaths in multiple sclerosis is believed to be mediated by autoreactive T-cells that target a specific autoantigen associated with the disease. This can be diagnosed according to embodiments described herein, for example, by detecting the mRNA sequences coding for the complementarity determining region 3 (CDR3) of the T-cell receptors specific to that autoantigen.

In some embodiments, the silencing target can be a marker or reporter molecule (e.g., GFP). In some embodiments, a silencing target may be used to inhibit or activate the expression a marker or reporter molecule (e.g., GFP), either in vitro or in vivo, in response to the presence of a detection target. Thus, methods disclosed herein can be used for detecting the presence of a detection target in a sample or cells.

Initiators

As discussed above, an initiator is a molecule that is able to interact with a detection target and subsequently expose an initiator region. The "activated initiator," i.e., one in which the initiator region has been exposed, can initiate formation of inactivator dsRNAs by initiating polymerization of monomers. In some embodiments, an activated initiator can initiate formation of inactivator dsRNAs by initiating further hybridization of monomers. One exemplary embodiment of an activated initiator is shown in, for example, FIG. 2C. Other exemplary embodiments of activated initiators are shown for example, in FIGS. 3-10.

In various embodiments, the initiator comprises a detection target binding region such that an initiator region of the initiator is made available when a predetermined physical event occurs. In the preferred embodiments, that predetermined event can be the presence of a detection target such as one associated with a disease, disorder or any undesirable state. In each of these embodiments, the initiator preferably comprises a molecule that is responsive to the presence of the detection target. In preferred embodiments, the initiator region of the initiator is made available in the presence of the detection target. For example, the initiator may comprise a molecule that undergoes a conformational change in response to binding to the detection target. The conformational change can expose the initiator region of the initiator, which can subsequently stimulate formation of the dsRNA substrates.

As described above, in some embodiments, the detection target binding region of the initiator is preferably at least 80%, more preferably at least 90%, 95% or higher, complementary to at least a portion of a detection target. In preferred embodiments, the detection target binding region is at least 2, 3, 4, 5, or 10 or more bases in length. Furthermore, in some embodiments, the initiator region of the initiator is preferably at least 80%, more preferably at least 90%, 95% or higher, complementary to an initiator complement region of a substrate monomer. In preferred embodiments, the initiator region is at least 2, 3, 4, 5, or 10 or more bases in length.

An aptamer is identified that is able to specifically bind a detection target molecule within a diseased cell. In some embodiments, the detection target binding region can be an aptamer.

The initiator preferably comprises a nucleic acid or other molecule that is able to contact a substrate monomer and trigger the formation of inactivator dsRNAs in the presence of a detection target. In some embodiments, the initiator comprises a sequence that is complementary to a portion, such as, for example without limitation, a sticky end, of a monomer, that is available for hybridization with the activated initiator while the monomer is in its kinetically stable state. In some embodiments, the initiator also preferably comprises a sequence that is complementary to a portion of the monomer adjacent to the sticky end such that hybridization of the monomer to the sticky end causes a conformational change in the monomer. For example, the initiator may comprise an initiator region that is complementary to the initiator complement region of a monomer, where the initiation region comprises a sticky end and a portion of a first stem region of the monomer adjacent to the sticky end, as described above and illustrated in FIG. 2B.

The structure of the initiator is preferably such that when the detection target is not present (or the other physical event has not occurred), the initiator region is not available to hybridize with an initiator complement region of a substrate monomer. The detection target frees the initiator region such that it can interact with an initiator complement region of a substrate monomer, triggering the formation of inactivator dsRNAs. In some embodiments, the detection target causes a conformational change in the initiator that allows the initiator to interact with the initiator complement region of a substrate monomer. Preferably, the initiator region is unavailable to hybridize to an initiator complement region unless the initiator is activated by binding to a detection target. In some embodiments, the initiator region of the initiator is substantially complementary to the initiator complement region of a substrate monomer. In some embodiments, the initiator complement region of a substrate monomer can comprise, for example, a sticky end and a portion of the first stem region of a substrate monomer.

In preferred embodiments, the initiator can comprise a detection target binding region that is complementary to an mRNA detection target sequence or a portion of an mRNA detection target sequence, for example, a portion of a mutant mRNA sequence that comprises a mutation associated with a disease or disorder. Embodiments also include specific combinations of mRNA sequences.

The initiator may comprise a nucleic acid initiator region that is linked to or associated with a recognition molecule, such as an aptamer, that is capable of interacting with a detection target. The initiator is designed such that the initiator region is unavailable to stimulate production of inactivator dsRNAs in the absence of the detection target. When the detection target interacts with the recognition molecule, the initiator region of the activated initiator is able to trigger RNAi. Preferably, the recognition molecule is one that is capable of binding the detection target.

Recognition molecules include, without limitation, polypeptides, antibodies and antibody fragments, nucleic acids, aptamers, and small molecules. The use of an initiator bound to an aptamer, where the aptamer serves as the detection target binding region.

Inactivator dsRNAs

In triggered RNAi, the silencing targets can be independent of the detection targets. Thus, triggered RNAi is considered an effective strategy for silencing genes in cells that contain a target molecule, where the target molecule may be unrelated to the gene that is silenced. Once an inactivator dsRNA forms within a target cell via the triggered RNAi mechanism, the inactivator dsRNA can lead to silencing of one or more desired silencing targets. This in turn, can modulate the expression of one or more marker or reporter molecules. In some embodiments, the inactivator dsRNA can be processed by Dicer, silencing of one or more desired silencing targets. Design of appropriate triggered RNAi hairpin monomers that do not themselves trigger RNAi in the absence of a detection target, but trigger RNAi upon binding a detection target, can be derived from detection target and silencing target sequences well known in the art and available from literature reviews and disclosed in, for example, various databases (e.g., NCBI).

The length and composition of the inactivator dsRNAs and RNA duplex substrates for Dicer can be controlled by the design of the substrate monomers used to form the inactivator dsRNAs. At least a portion of the inactivator dsRNA sequence is preferably homologous to at least a portion of the silencing target sequence. In some embodiments, the inactivator dsRNA formed is a RISC substrate that bypasses dicer action.

Design of RNA duplex substrates for Dicer is described in, for example, Amarzguioui et al., 2006, Nature Protocols 1, 508-517 and Vermeulen et al., 2005, RNA 11(5): 674-682. In some embodiments, the length of the RNA duplex substrate formed by substrate monomers is from about 12 to about 100 bp. In some embodiments, the length of the RNA duplex substrate formed by substrate monomers is from about 23 to about 30 bp. In some embodiments, the RNA duplex substrate can be about 25 to about 27 bp. In some embodiments, the RNA duplex substrate can be at least 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length. In some embodiments, the RNA duplex substrate can be a blunt 27-mer duplex. In some embodiments, the RNA duplex substrate can comprise a single 2-base 3'-overhang. In some embodiments, the RNA duplex substrate can comprise a combination of a single 2-base 3'-overhang on one end and DNA bases on the opposing blunt end. In some embodiments, the RNA duplex substrate can comprise a single 1, 2, 3, 4 or 5-base 3'-overhang. RNA monomers may be designed to produce RNA duplex substrates, for example, by designing two complementary RNA strands where one strand has two additional non-complementary base pairs at an end.

In some embodiments, the RNA duplex substrate can comprise a 3'-overhang on the antisense. In some embodiments, the RNA duplex substrate can comprise a 3'-overhang resides on the sense (S) strand. In some embodiments, processing of the RNA duplex by Dicer can produce siRNAs comprising, for example, 21-nt passenger and guide strands that form a 19 bp duplex with 2-nt 3' overhangs. See, e.g., Kim et al., 2007, Nature Reviews Genetics 8(3): 711-719. In some embodiments, processing of the RNA duplex by Dicer can produce siRNAs comprising, for example, 21-nt passenger and guide strands that form a 10, 11, 12, 13, 14, 15, 16, 17, 18, 19, 20 or 21-bp duplex with 0, 1, 2, 3, 4, 5-nt 3' overhangs.

In some embodiments, the inactivator dsRNAs can be about 17 to about 27 bp long. In some embodiments, the inactivator dsRNAs can be about 25 to about 27 bp long. In some embodiments, the inactivator dsRNAs can comprise two 21-nt strands that form a 19 bp duplex with 2-nt 3' overhangs. In some embodiments, the inactivator dsRNAs can comprise two 21-nt strands that form a 10, 11, 12, 13, 14, 15, 16, 17, 18, 19, 20 or 21-bp duplex with 0, 1, 2, 3, 4, 5-nt 3' overhangs. In some embodiments, the inactivator can comprise an RNA duplex of about 10 to about 100 bases pairs with about 0 to about 100 nucleotides overhangs on any or all of the 3' and 5' ends of the duplex.

Gene Silencing Using Triggered RNAi

Because the silencing targets are independent of the detection targets, triggered RNAi is considered an effective strategy for silencing genes in cells containing a particular detection target by forming inactivator dsRNA which silences an independent gene. Once an inactivator dsRNA forms within a target cell, the inactivator dsRNA substrate leads to silencing of one or more silencing targets. In some embodiments, the inactivator dsRNA can be processed by Dicer, leading to subsequent silencing of desired silencing target(s). Design of appropriate triggered RNAi monomers that do not themselves trigger RNAi, but trigger RNAi upon binding a detection target, can be derived from detection target and silencing target sequences well known in the art and available from literature reviews and disclosed in, for example, various databases (e.g. NCBI).

Triggered RNAi can be performed, for example, using RNA hairpin monomers and/or complexed monomers (complexes) to detect a detection target, such as a target associated with a disease or a disorder and subsequently silence an independent silencing target. In some embodiments, the detection target can be associated with a cellular membrane. In other embodiments, the detection target can be a non-tethered entity. The detection target can be, for example, a nucleic acid associated with cancer, such as an mRNA associated with a cancer. In various embodiments, an RNA hairpin initiator with an initiator region hybridizes or binds the detection target. Binding of the detection target to the initiator causes a conformational change of the initiator and exposes the initiator region. Hybridization between the initiator complement region of a first substrate monomer and the exposed initiator region of the activated initiator causes a conformational change of the first substrate monomer to expose a sequence that is substantially complementary to the silencing target region of a second substrate monomer.

Hybridization between the exposed sequence of the first substrate monomer and the silencing target region of the second substrate monomer causes a conformational change of a second substrate monomer. This event forms an inactivator dsRNA. In some embodiments, the inactivator dsRNA can be a substrate for Dicer. Dicer can process the dsRNA substrate into siRNAs, which associate with the RISC complex and subsequently silence one or more silencing target. In other embodiments, the inactivator dsRNA is not processed by Dicer, but can still lead to silencing of one or more silencing targets. For example, the inactivator dsRNA can itself serve as a RISC substrate (e.g., as siRNA). The triggered RNAi action can lead to, for example, modulation of expression of a marker or reporter molecule (e.g., GFP).

In some embodiments, triggered RNAi c an be used to diagnose a disease or disorder in a subject. Because triggered RNAi can be specifically limited to those cells containing the detection target associated with the disease or disorder, the triggered RNAi monomers can be delivered to a multitude of cells, including healthy cells. Thus, general delivery of the monomers to a population of cells comprising cells containing a disease-associated detection target and wild-type cells is possible. Triggered RNAi takes place in diseased cells containing the detection target, leading to the silencing of one or more silencing targets in cells in diagnostic applications.

Delivery of Triggered RNAi Monomers Markers, and Initiators to Target Cells

Initiators, triggered RNAi monomers, complexed monomers (complexes), marker genes, and any accessory molecules, such as, for example, helper molecules, can be formulated with any of a variety of carriers well known in the art to facilitate introduction into a sample (e.g., cells). Suitable carriers for delivery of nucleic acids to cells are well known in the art and include, for example, polymers, proteins, carbohydrates and lipids. For example, a cyclodextrin-containing polymer can be used for the delivery of the triggered RNAi monomers. Commercial transfection reagents known in the art, such as, for example, LNCaP (Altogen Biosystems) or lipofectamine RNAiMax (Invitrogen), can be used.

Delivery of nucleic acids can be accomplished, for example, as described by Heidel (Heidel, J. D. 2005. Targeted, systematic non-viral delivery of small interfering RNA in vivo. Doctoral thesis, California Institute of Technology. 128p., herein incorporated by reference in its entirety). Also contemplated within the scope of the subject matter are gene delivery systems as described by Feigner et al. (Feigner et al. 1997. *Hum Gene Ther* 8:511-512, herein incorporated by reference in its entirety), including cationic lipid-based delivery systems (lipoplex), polycation-based delivery systems (polyplex) and a combination thereof (lipopolyplex). Cationic lipids are described, for example, in U.S. Pat. Nos. 4,897,355 and 5,459,127, each of the foregoing which is herein incorporated by reference in its entirety. Proteins can also be used for HCR delivery, such as synthetic neoglycoproteins (Ferkol et al. 1993. *FASEB J* 7:1081-1091; Perales et al. 1994. *Proc Nat Acad Sci* 91:4086-4090; each of which is incorporated herein by reference in its entirety). epidermal growth factor (EGF) (Myers, EPO 0273085, incorporated herein by reference in its entirety), and other ligands for receptor-mediated gene transfer (Wu and Wu. 1987. *J Biol Chem* 262(10):4429-4432; Wagner et al. 1990. *Proc Natl Acad Sci USA* 87(9):3410-3414; Ferkol et al. 1993. *J Clin Invest* 92(5):2394-2300; Perales et al. 1994. *Proc Natl Acad Sci USA* 91(9):4086-4090; Myers, EPO 0273085; each of which is incorporated herein by reference in its entirety).

Viral and viral vector-like delivery systems generally known in the art, such as those described, for example, in U.S. Pat. Nos. 7,0333,834; 6,899,871; 6,555,367; 6,485,965; 5,928,913; U.S. patent application Ser. No. 10/801,648; U.S. patent application Ser. No. 10/319,074, and U.S. patent application Ser. No. 09/839,698, each of which is herein incorporated by reference, are also contemplated for use in the present subject matter. In addition, standard electroporation techniques can be readily adopted to deliver HCR monomers.

Delivery of triggered RNAi monomers and/or marker or reporter molecules can occur in vivo or ex vivo. In some embodiments, cells can be removed from a patient and transfected with the monomers. In other embodiments, triggered RNAi monomers and/or marker or reporter molecules can be delivered to cells in vivo such as by, for example, injection of the monomers within a delivery vehicle into the bloodstream or by intramuscular, subcutaneous, or intraperitoneal means. An appropriate means of delivering triggered RNAi monomers and/or marker or reporter molecules to a desired population of cells can be identified by the skilled practitioner based on the particular circumstances without undue experimentation.

Initiation of Triggered RNAi

Activated initiators can serve as initiators of triggered RNAi. In embodiments based on detection of a disease-associated mRNA sequence, an initiator can be designed that only initiates formation of inactivator dsRNAs in the presence of the detection target mRNA sequence. If an mRNA detection target sequence is chosen that is only expressed in certain types of cells e.g. cells with a particular genetic mutation or nucleic acid signature, then triggered RNAi will only occur in the cells expressing the target sequence. Polymerization of triggered RNAi monomers will not occur in cells without the detection target mRNA sequence. Triggered RNAi creates inactivator dsRNAs, which leads to silencing of one or more silencing targets.

Detection targets contemplated for triggered RNAi include those associated with a disease or disorder, as well as other non-disease associated targets, such as a cell-type marker, as described herein and in the art. In some embodiments the detection target is a nucleic acid that is to be detected in a sample or a portion of a nucleic acid that is to be detected. In this case, the sequence of the detection target nucleic acid is taken into consideration in designing the triggered RNAi monomers and/or complexes. In some embodiments, the detection target can be a nucleic acid signature or specific mutation in a genetic sequence associated with a disease or disorder. Genetic mutations include, but are not limited to, point mutations, non-native genetic fusions, deletion of at least one base, insertion of at least one base, frame-shift mutations, and inversions. In other embodiments, the detection target is a combination of nucleic acid molecules associated with a disease or disorder.

Detection targets for triggered RNAi also include, but are not limited to, nucleic acid molecules, proteins, peptides, carbohydrates, lipids and small molecules. In preferred embodiments, the detection target binds a molecule, an initiator, which can initiate formation of inactivator dsRNAs. In some embodiments, the detection target can initiate formation of inactivator dsRNAs by, for example, binding directly to a substrate monomer.

Where the disease to be diagnosed is a cancer, an mRNA detection target is typically one expressed in cancer cells and not in healthy cells or at least to a lesser extent in healthy cells. In some cases, a disease may be identified by the expression of several mRNA detection targets simultaneously. In this case, the triggered RNAi initiator sequence can be designed, for example, to initiate triggered RNAi only in the event that a specific combination of mRNAs is detected, for example, by detecting a portion of an mRNA fusion entity.

In some embodiments, triggered RNAi can be performed with RNA monomers instead of, or in conjunction with, DNA monomers. In some embodiments, triggered RNAi can be performed with RNA-DNA hybrid monomers. In some embodiments, RNAi can be performed with, for example, RNA hairpins with stems of approximate length 14 and loops of approximate length 4, which exhibit similar properties to DNA hairpins with stems of approximate length 18 and loops of approximate length 6. Stems and loops of other lengths are also possible.

The concentration of the monomers can be adjusted to ensure that a sufficient amount of inactivator dsRNA is produced to effectively silence one or more silencing targets. Because of the self-propagating nature of the reaction, each copy of the detection target can begin the formation of inactivator dsRNAs. Furthermore, recycling of an activated initiator molecule allows catalytic amplification of the initial detection target binding event. In a catalytic triggered RNAi scheme, the amount of inactivator dsRNA can be higher than the amount of detection target due to catalytic turnover of the activated initiator. Thus, the amount of detection target does not have to equal the amount of silencing target in order to achieve gene silencing, because each detection target can lead to silencing of multiple silencing targets. The embodiment depicted in FIGS. 2 and 3 is catalytic and hence amplifies the signal provided by the detection target to achieve sufficient amounts of inactivator dsRNA.

In some embodiments, triggered RNAi monomers can be used in conjunction with nucleic acid "helper" monomers to facilitate detection target recognition. In preferred embodiments, the nucleic acid "helper" monomers are DNA molecules. Triggered RNAi can be more difficult to initiate with a long mRNA or other nucleic acid detection target because secondary structure within the mRNA strand reduces accessibility of the target site, i.e., the portion of the detection target recognized by the detection target binding region, to the triggered RNAi monomers. The use of DNA "helper" monomers that bind to regions flanking the target site helps eliminate competing secondary structures that form between the target site and the flanking regions. RNAi is more effectively initiated as a result of the elimination of secondary structure formation within the detection target mRNA strand. Helper DNA strands can be from about 10 to about 100 bases in length. In some embodiments, the helper DNA strands are from about 10 to about 75 bases in length. In other embodiments, the helper DNA strands are from about 10 to about 50 bases in length. In other embodiments, the helper DNA strands are from about 10 to about 35 bases in length. In preferred embodiments, the helper DNA strands are from about 10 to about 25 bases in length.

In some embodiments, RNA monomers are used in conjunction with an initiator comprising a DNA probe molecule that contains an initiator region. The initiator region is exposed upon binding between the DNA probe molecule and an mRNA molecule detection target and subsequently initiates formation of inactivator dsRNA substrates. Single stranded regions on either side of the duplex region of the DNA probe compete with native base pairing within the detection target molecule to initiate the RNAi process.

The design of the triggered RNAi monomers can be adjusted such that they bind specifically to nucleic acid detection targets, mRNA or otherwise. In addition, the design of the substrate monomers can be adjusted such that they specifically silence one or more silencing targets. The design can be derived from sequences derived from literature reviews and disclosed in, for example, various databases (e.g., NCBI).

Compositions and Kits for Triggered RNAi and Diagnosis

Compositions and kits for triggered RNAi are contemplated for use within the scope of the subject matter. In some embodiments, the compositions comprise an initiator monomer (initiator), a first substrate monomer, a second substrate monomer, and a marker gene. In some embodiments, the compositions comprise an initiator hairpin monomer, a first substrate monomer, a second substrate monomer, and a marker gene. In some embodiments, the compositions comprise an initiator hairpin monomer, a first RNA hairpin substrate monomer, a second RNA hairpin substrate monomer, and a marker gene. In some embodiments, the compositions comprise an initiator monomer, a first substrate complex, a second substrate complex, and a marker gene. In some embodiments, the compositions comprise an initiator monomer, a first substrate monomer, and a marker gene. Upon delivery to a target cell or sample and recognition of the detection target by the initiator, triggered RNAi is initiated causing the formation of inactivator dsRNAs and subsequent silencing of one or more silencing targets. The silencing of one or more silencing targets modulates the expression of one or more marker genes.

The compositions can also contain other components, such as, for example, accessory molecules that facilitate detection target recognition and aid the formation of initiator dsRNAs. Accessory molecules typically comprise nucleic acid molecules. In some embodiments, the accessory molecules are DNA helper strands that bind to regions flanking a detection target nucleic acid sequence. Preferably the accessory molecules are DNA helper strands that bind to regions flanking the initiator binding site on a detection target.

Furthermore, the composition can comprise a carrier that facilitates the introduction of nucleic acids, such as, for example, RNA monomers and accessory nucleic acid molecules, into a cell, such as a cell containing a detection target associated with a disease or disorder. Carriers for delivery of nucleic acids into cells are well known in the art and examples are described above.

A kit for triggered RNAi typically comprises the compositions as described in detail above. In some embodiments the kits comprise an initiator monomer (initiator) and one or more monomers or complexes. In some embodiments, the kits comprise an initiator monomer and a first substrate monomer. In some embodiments, the kits comprise an initiator monomer, a first substrate monomer and a second substrate monomer. In some embodiments, the kits comprise an initiator monomer, a first substrate complex and a second substrate complex. In some embodiments, the kits further comprise one or more marker genes. In preferred embodiments, the kit is used to deliver triggered RNAi monomers and/or complexes and the marker gene(s) to a population of cells comprising cells comprising a disease-associated detection target as well as healthy, wild-type cells. In some embodiments, the kit is used to deliver RNAi monomers and marker gene(s) to the tissues of a patient, wherein the tissues comprise cells comprising a detection target associated with a disease or disorder. In other embodiments, the kit is used to select for cells containing a detection target in vitro.

In some embodiments, the kit includes a vector (e.g., a plasmid) comprising a GFP coding sequence, and optionally a vector (e.g., a plasmid) comprising a repressor coding sequence, and monomer specific for a particular detection target. In some embodiments one vector can comprise the GFP coding sequence and the repressor coding sequence.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Triggered RNAi for Inactivation of Target Gene in the Presence of a Detection Target Associated with a Disease This example illustrates the use of RNAi to silence a target gene in the presence of a detection target.

Triggered RNAi can be used to silence a target gene by designing first, second and third monomers of a triggered RNA system to detect a detection target associated with a disease, or a cell type associated with a disease, and subsequently silence a target gene to diagnose a disease or disorder. Examples of triggered RNAi mechanisms are illustrated in FIGS. 2-10. For the basic triggered RNAi system illustrated in FIGS. 2 and 3, stock solutions can be prepared as follows: monomer 1 (hereinafter the "initiator", depicted as "A" of FIG. 2A), monomer 2 (hereinafter the "first substrate monomer", depicted as "B" of FIG. 2E), and monomer 3 (hereinafter the "second substrate monomer", depicted as "C" of FIG. 2G), disease-associated detection target mRNA (either "detection target" comprising only a detection target sequence without flanking regions or "detection target fusion" comprising the detection target sequence with flanking regions), mRNA 1 ("healthy mRNA 1"), mRNA 2 ("healthy mRNA 2"), silencing target mRNA ("silencing target") and helper DNA ("D1" and "D2" annealed together in one solution). Reactions can be set up by combining the triggered RNAi monomers, helper DNA, and detection and silencing targets. The formation of inactivator dsRNAs and degradation of silencing target mRNA occurs in samples containing the disease-associated target mRNA, but not samples containing only healthy mRNAs. The degradation of silencing target mRNA modulates one or more marker or reporter molecules (e.g., GFP). The samples can be analyzed by a variety of methods known in the art for the presence of the marker or reporter molecules.

The initiator, first substrate monomer, second substrate monomer, and marker molecule are delivered to target cells using standard gene delivery methods. In the presence of the detection target, production of inactivator dsRNAs sufficient for silencing the silencing target is initiated. The inactivator dsRNAs silence the silencing target, thereby inactivating the silencing target gene. The degradation of silencing target mRNA modulates one or more marker or reporter molecules (e.g., GFP).

Example 2

In Vivo Triggered RNAi Diagnosis of Diseases Caused by Fused Gene Mutations

Two or more genes are fused together to encode an oncogenic protein (Dohjima, T. et al. *Molecular Therapy* 7: 811-816 (2003), herein incorporated by reference in its entirety). Although the two or more genes are present in healthy cells, the overlap region between the genes is a distinct signature found only in tumor cells. Triggered RNAi hairpin monomers are designed to form inactivator dsRNAs in the presence of a detection target sequence included within the overlap region. The hairpin monomers include an initiator and substrate monomers. The hairpin monomers have stems ranging in length between 10 and 35 base pairs. The hairpin monomers are introduced in vivo into tumor cells or in vitro into tumor samples by gene delivery methods known in the art. Recognition of the detection target by the initiator hairpin monomer activates the initiator, and the activated initiator initiates formation of inactivator dsRNAs. Inactivator dsRNAs are produced in the target cells, i.e., cells having the detection target. The inactivator dsRNAs are processed by Dicer to produces siRNAs. The siRNAs associate with RISC and subsequently inactivates one or more genes, which modulates a reporter molecule (e.g., GFP). The triggering of this response can diagnose diseased samples (e.g., cells).

Example 3

Triggered RNAi-Aptamer Diagnosis of Disease

RNAi hairpin monomers are designed that link the aptamer to a hairpin monomer in such a way that in the absence of the detection target, the aptamer does not allow conformational change of the hairpin monomer and does not initiate formation of inactivator dsRNAs. The triggered RNAi hairpin monomers are introduced in vivo or in vitro into a sample (e.g., cells) by gene delivery methods known in the art. Recognition between the aptamer and the detection target allows conformational change of the hairpin monomer and exposes an initiator region. The initiator region can initiate production of an inactivator dsRNA in the target cells. The inactivator dsRNAs are processed by Dicer to produce siRNAs. The siRNAs associate with RISC and subsequently inactivates one or more genes, which modulates a reporter molecule (e.g., GFP). The triggering of this response can diagnose diseased samples (e.g., cells).

Example 4

Triggered RNAi Modulation of Green Fluorescent Protein (GFP)

This example illustrates the modulation of a reporter molecule signal in the presence of a detection target. Triggered RNAi monomers are added to samples. The samples can be in vitro samples or, triggered RNAi monomers can be delivered to target cells using standard gene delivery methods. In the presence of a detection target, production of inactivator dsRNAs is initiated. The inactivator dsRNAs modulate GFP mRNA levels. Thus, the presence of a detection target changes the fluorescence emission of the GFP.

Example 5

Triggered RNAi Silencing of GFP mRNA

This example illustrates the silencing of a reporter molecule signal in the presence of a detection target. Triggered RNAi monomers are added to samples. The samples can be in vitro samples or, triggered RNAi monomers can be delivered to target cells using standard gene delivery methods. In the presence of a detection target, production of inactivator dsRNAs is initiated. The inactivator dsRNAs modulate GFP mRNA levels by silencing GFP mRNA. Thus, the presence of a detection target reduces the fluorescence emission of the GFP.

Example 6

GFP Silencing by siRNAs and Non-Canonical Dicer Substrates

Figure 12:
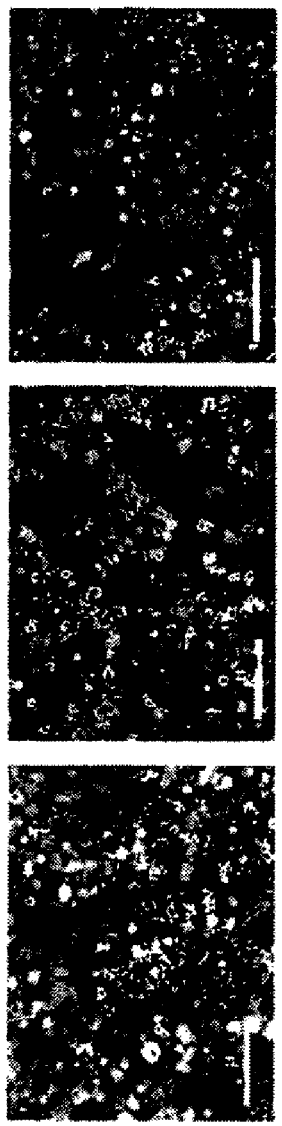
FIG. 12 illustrates an example of an application of a triggered RNAi system. The experiment conducted in FIG. 12 demonstrates GFP silencing in mammalian cells via siRNA and non-canonical Dicer substrates.

This example demonstrates that non-canonical Dicer substrates can achieve gene silencing in mammalian cells. P in FIG. 12 denotes a 5' phosphate group. 500 ng of GFP plasmid (pRetroQ-AcGFP1, Clontech) and 500 ng of RFP plasmid (pDsRed2-C1, Clontech) were cotransfected via Lipofectamine 2000 (Invitrogen) into each well of a 6-well plate (BD-Falcon) containing HEK 293A cells (Invitrogen). The co-transfection mixture also included either 20 pMol siRNA (19-bp duplex with 2-nt 3' overhangs), non-canonical Dicer substrate (incorporating a 23-bp duplex) or opti-mem I reduced serum medium (Gibco). The transfected cells were incubated at 37° C. with 5% $CO_2$, and then imaged, 24 hours post transfection, using an Axio Observer Z1 (Zeiss) inverted fluorescence microscope. The results are illustrated in FIG. 12. FIG. 12 demonstrates that both traditional siRNAs and non-canonical Dicer substrates with a 23-bp duplex region and long tails achieve potent and specific silencing of GFP in HEK 293A cells. Introducing non-canonical Dicer substrates with long tails and 19 bp, 21 bp, or 25 bp RNA duplexes also induced potent and specific GFP silencing.

While the present teachings have been described in terms of these exemplary embodiments, the skilled artisan will readily understand that numerous variations and modifications of these exemplary embodiments are possible without undue experimentation. All such variations and modifications are within the scope of the current teachings.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein.

Incorporation By Reference

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

Equivalents

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A method of detecting the presence of a detection target by modulating the expression of a marker gene, the method comprising:
    providing an initiator to a cell, wherein the cell comprises a detection target, a silencing target gene, and a marker gene, wherein the detection target is different from the silencing target gene, wherein the initiator comprises a nucleic acid sequence comprising a) a detection binding region that binds to the detection target and b) an initiator region;
    providing a first substrate monomer to the cell, wherein the first substrate monomer comprises a silencing target complement region that is substantially complementary to a portion of the silencing target gene, and an initiator complement region, wherein the initiator complement region hybridizes to the initiator region; and
    providing a second substrate monomer to the cell, wherein the second substrate monomer comprises a silencing target region that is substantially complementary to the silencing target complement region, wherein binding of the detection target to the initiator initiates hybridization of the silencing target complement region of the first substrate monomer to the silencing target region of the second substrate monomer and formation of an inactivator double-stranded RNA (inactivator dsRNA) which silences the silencing target gene, and wherein said silencing of the silencing target gene modulates the expression of said marker gene;
    determining the level of expression of said marker gene; and
    assessing whether said maker gene is expressed at a level that is different than a predetermined level, thereby detecting the presence of said detection target.

2. The method of claim 1, wherein upon binding of the detection target to the initiator, a portion of the initiator is made available to bind to the initiator complement region of the first substrate monomer.

3. The method of claim 2, wherein upon binding of the initiator complement region to the initiator, the silencing target complement region is made available to bind to the silencing target region of the first substrate monomer.

4. The method of claim 3, wherein upon binding of the silencing target region to the silencing target complement region, the inactivator dsRNA is formed.

5. The method of claim 1, wherein the initiator comprises an RNA hairpin monomer.

6. The method of claim 1, wherein the nucleic acid sequence comprises a conformation-switching aptamer.

7. The method of claim 1, wherein the first substrate monomer is an RNA hairpin.

8. The method of claim 1, wherein the second substrate monomer is an RNA hairpin.

9. The method of claim 1, further comprising: contacting the cell with at least one accessory molecule comprising a nucleic acid sequence that binds to a region flanking the initiator binding site of the detection target.

10. The method of claim 1, wherein the initiator region is able to bind to the initiator complement region when a detection target is present in the cell.

11. The method of claim 1, wherein the inactivator dsRNA can be processed by Dicer.

12. The method of claim 11, wherein the inactivator dsRNA can be processed to produce a 19 bp duplex with 2-nt 3' overhangs.

13. The method of claim 11, wherein the inactivator dsRNA comprises a RNA duplex substrate from about 19 base pairs to about 22 base pairs in length.

14. The method of claim 1, wherein the inactivator dsRNA is an siRNA.

15. The method of claim 14, wherein the inactivator dsRNA is a 19 bp duplex with 2-nt 3' overhangs.

16. The method of claim 1, wherein the marker gene is GFP.

17. The method of claim 1, wherein the detection target is a nucleic acid.

18. The method of claim 17, wherein the silencing target gene is an mRNA comprising a sequence different from the sequence of the detection target.

19. The method of claim 1, wherein the detection target is associated with a disease or disorder.

20. The method of claim 19, wherein the detection target is an mRNA associated with a cancer.

21. The method of claim 19, wherein the detection target is a viral nucleic acid.

22. The method of claim 19, wherein the detection target is an mRNA molecule associated with a disease or disorder.

23. The method of claim 1, wherein the silencing target gene is an mRNA.

24. The method of claim 1, wherein the silencing target gene comprises said marker gene.

25. The method of claim 1, wherein the silencing target gene comprises a nucleic acid sequence that modulates the expression of said marker gene.

26. The method of claim 1, wherein the initiator comprises a recognition molecule such that upon binding of the recognition molecule to the detection target, a portion of the initiator is made available to bind to the initiator complement region of the first substrate monomer.

27. The method of claim 26, wherein the recognition molecule is an aptamer.

28. The method of claim 26, wherein the detection target is a nucleic acid.

29. The method of claim 26, wherein the detection target is selected from the group consisting of polypeptides, carbohydrates, lipids and small molecules.

30. A method of detecting the presence of a detection target by modulating the expression of a marker gene, the method comprising:

contacting a cell with an initiator, wherein the cell comprises a detection target, a silencing target gene, and a marker gene, wherein the initiator comprises a nucleic acid sequence comprising a detection target binding region, an initiator region, and a silencing target complement region, wherein the detection target binding region can interact with the detection target, and wherein the detection target is different from the silencing target gene; and contacting the cell with a substrate monomer comprising a nucleic acid that is at least partially double stranded, wherein the substrate monomer comprises an initiator complement region that is complementary to the initiator region of the initiator and a silencing target region that is complementary to the silencing target complement region, wherein an inactivator double-stranded RNA (inactivator dsRNA) is formed by hybridization of the silencing target complement region to the silencing target region subsequent to interaction of the detection target to the detection target binding region, wherein the inactivator dsRNA silences the silencing target gene, and wherein said silencing of the silencing target gene modulates the expression of said marker gene;

determining the level of expression of said marker gene; and assessing whether said maker gene is expressed at a level that is different than a predetermined level, thereby detecting the presence of said detection target.

* * * * *

UNITED STATES PATENT AND TRADEMARK OFFICE
CERTIFICATE OF CORRECTION

PATENT NO. : 8,241,854 B2
APPLICATION NO. : 12/454743
DATED : August 14, 2012
INVENTOR(S) : Peng Yin et al.

It is certified that error appears in the above-identified patent and that said Letters Patent is hereby corrected as shown below:

Column 1, Line 13, under Statement Regarding Federally Sponsored R&D, please remove "This invention was made with government support under grant nos. NIH 5R01EB006192-04 "Hybridization chain reaction: in situ amplification for biological imaging" and NIH P50 HG004071 "Center for in toto genomic analysis of vertebrate development"." and insert therefore, --This invention was made with government support under Grant No. HG004071 awarded by the National Institutes of Health. The government has certain rights in the invention.--.

Signed and Sealed this
Twenty-fifth Day of September, 2012

David J. Kappos
*Director of the United States Patent and Trademark Office*

UNITED STATES PATENT AND TRADEMARK OFFICE
CERTIFICATE OF CORRECTION

PATENT NO. : 8,241,854 B2  
APPLICATION NO. : 12/454743  
DATED : August 14, 2012  
INVENTOR(S) : Peng Yin et al.

Page 1 of 1

It is certified that error appears in the above-identified patent and that said Letters Patent is hereby corrected as shown below:

Specification

At Column 1, Line 13, under STATEMENT REGARDING FEDERALLY SPONSORED R&D, please remove "This invention was made with government support under Grant No. HG004071 awarded by the National Institutes of Health. The government has certain rights in the invention."

and insert therefore,

-- This invention was made with government support under Grant Nos. HG004071 and CA140759 awarded by the National Institutes of Health. The government has certain rights in the invention. --.

Signed and Sealed this
Seventeenth Day of November, 2015

Michelle K. Lee
*Director of the United States Patent and Trademark Office*